(12) United States Patent
Liang et al.

(10) Patent No.: US 8,415,165 B2
(45) Date of Patent: Apr. 9, 2013

(54) SYSTEM AND METHOD FOR AUTHENTICATING SPORTS IDENTIFICATION GOODS

(75) Inventors: Ming-Hwa Liang, Stony Brook, NY (US); Stephane Shu Kin So, Stony Brook, NY (US); James Hayward, Stony Brook, NY (US)

(73) Assignee: APDN (B.V.I.), Inc., Stony Brook, NY (US)

( * ) Notice: Subject to any disclaimer, the term of this patent is extended or adjusted under 35 U.S.C. 154(b) by 860 days.

(21) Appl. No.: 11/954,051

(22) Filed: Dec. 11, 2007

(65) Prior Publication Data

US 2008/0293052 A1    Nov. 27, 2008

Related U.S. Application Data

(63) Continuation-in-part of application No. 11/437,265, filed on May 19, 2006, which is a continuation-in-part of application No. 10/825,968, filed on Apr. 15, 2004.

(60) Provisional application No. 60/682,976, filed on May 20, 2005, provisional application No. 60/463,215, filed on Apr. 16, 2003, provisional application No. 60/874,425, filed on Dec. 12, 2006, provisional application No. 60/877,875, filed on Dec. 29, 2006, provisional application No. 60/877,869, filed on Dec. 29, 2006.

(51) Int. Cl.
*G01N 33/00* (2006.01)
*C12Q 1/68* (2006.01)

(52) U.S. Cl. ............ 436/91; 436/94; 436/164; 252/582; 435/6.11; 442/121

(58) Field of Classification Search .................... 436/91, 436/94, 164; 252/582; 435/6.11; 442/121
See application file for complete search history.

(56) References Cited

U.S. PATENT DOCUMENTS

| 4,183,989 A | 1/1980 | Tooth |
| 4,739,044 A | 4/1988 | Stabinsky |

(Continued)

FOREIGN PATENT DOCUMENTS

| EP | 1403335 A1 | 3/2004 |
| GB | 2434570 | 8/2007 |

(Continued)

OTHER PUBLICATIONS

Wollenberger, L.V. Detection of DNA using upconverting phosphor reporter probes.(1997). Proceedings of SPIE—The International Society for Optical Engineering, 2895(Ultrasensitve Biochemical Diagnostics II), 100-111.*

(Continued)

*Primary Examiner* — Krishnan S Menon
*Assistant Examiner* — Rebecca M Fritchman
(74) *Attorney, Agent, or Firm* — Algis Anilionis; F. Chau & Associates LLC

(57) ABSTRACT

A method for authenticating and verifying garment to be genuine is described. The method for authenticating a garment comprises applying a particular nucleic acid material/marker associated with a particular sequence of nucleic acid bases to a dye or paint and applying the marker to the garment. The method also comprises collecting a sample from the garment and verifying the garment is genuine by detecting the particular nucleic acid material on or within the garment.

45 Claims, 4 Drawing Sheets

U.S. PATENT DOCUMENTS

| | | | |
|---|---|---|---|
| 4,757,141 | A | 7/1988 | Fung et al. |
| 5,047,519 | A | 9/1991 | Hobbs, Jr. et al. |
| 5,132,242 | A | 7/1992 | Cheung |
| 5,139,812 | A | 8/1992 | Lebacq |
| 5,151,507 | A | 9/1992 | Hobbs, Jr. et al. |
| 5,429,952 | A | 7/1995 | Garner et al. |
| 5,602,381 | A | 2/1997 | Hoshino et al. |
| 5,639,603 | A | 6/1997 | Dower et al. |
| 5,763,176 | A | 6/1998 | Slater et al. |
| 5,776,713 | A | 7/1998 | Garner et al. |
| 5,866,336 | A | 2/1999 | Nazarenko et al. |
| 5,942,444 | A | 8/1999 | Rittenburg et al. |
| 5,989,823 | A | 11/1999 | Jayasena et al. |
| 6,030,657 | A | 2/2000 | Butland et al. |
| 6,057,370 | A | 5/2000 | Weiland et al. |
| 6,127,120 | A | 10/2000 | Graham et al. |
| 6,140,075 | A | 10/2000 | Russell et al. |
| 6,169,174 | B1 | 1/2001 | Hasegawa et al. |
| 6,312,911 | B1 | 11/2001 | Bancroft et al. |
| 6,342,359 | B1 | 1/2002 | Lee et al. |
| 6,399,397 | B1 | 6/2002 | Zarling et al. |
| 6,576,422 | B1 | 6/2003 | Weinstein et al. |
| 6,686,149 | B1 | 2/2004 | Sanchis et al. |
| 6,743,640 | B2 | 6/2004 | Whitten et al. |
| 6,995,256 | B1 | 2/2006 | Li et al. |
| 7,060,874 | B2 | 6/2006 | Wilkins |
| 7,115,301 | B2 | 10/2006 | Sheu et al. |
| 7,160,996 | B1 | 1/2007 | Cook |
| 7,223,906 | B2 | 5/2007 | Davis |
| 2002/0048822 | A1 | 4/2002 | Rittenburg et al. |
| 2002/0056147 | A1* | 5/2002 | Dau et al. ............ 800/8 |
| 2002/0187263 | A1 | 12/2002 | Sheu et al. |
| 2003/0142704 | A1 | 7/2003 | Lawandy |
| 2003/0142713 | A1 | 7/2003 | Lawandy |
| 2003/0162296 | A1 | 8/2003 | Lawandy |
| 2003/0177095 | A1 | 9/2003 | Zorab et al. |
| 2004/0063117 | A1 | 4/2004 | Rancien et al. |
| 2004/0166520 | A1 | 8/2004 | Connolly |
| 2004/0219287 | A1 | 11/2004 | Regan et al. |
| 2005/0059059 | A1 | 3/2005 | Liang |
| 2005/0214532 | A1 | 9/2005 | Kosak et al. |
| 2006/0017957 | A1 | 1/2006 | Degott et al. |
| 2006/0017959 | A1 | 1/2006 | Downer et al. |
| 2006/0117465 | A1 | 6/2006 | Willows et al. |
| 2006/0121181 | A1 | 6/2006 | Sleat et al. |
| 2006/0286569 | A1 | 12/2006 | Bar-Or et al. |
| 2007/0048761 | A1 | 3/2007 | Reep et al. |

FOREIGN PATENT DOCUMENTS

| | | |
|---|---|---|
| RU | 2170084 C1 | 10/2001 |
| WO | WO 87/06383 | 10/1987 |
| WO | WO 9014441 | 11/1990 |
| WO | WO 9502702 A1 | 1/1995 |
| WO | WO 9506249 | 3/1995 |
| WO | WO 97/45539 A1 | 12/1997 |
| WO | WO 98/06084 A1 | 2/1998 |
| WO | WO 9959011 | 11/1999 |
| WO | WO 00/55609 A2 | 9/2000 |
| WO | WO 01/25002 A1 | 4/2001 |
| WO | WO 0199085 A1 | 12/2001 |
| WO | WO 02057548 A1 | 7/2002 |
| WO | WO 03/030129 A2 | 4/2003 |
| WO | WO 03080931 A1 | 10/2003 |
| WO | WO 2004/025562 A1 | 3/2004 |
| WO | WO 2004025562 A1 | 3/2004 |
| WO | WO 02/084617 A1 | 7/2008 |

OTHER PUBLICATIONS

Zuckermann, et al. "Efficient methods for attachment of thiol specific probes to the 3'-ends of synthetic oligodeoxyribonucleotides." Nucleic Acids Research, vol. 15, pp. 5305-5321 (1987). IRL Press Limited, Oxford, England.

Gupta, et al. "A general method for the synthesis of 3'-sulfhydryl and phosphate group containing oligonucleotides." Nucleic Acids Research, vol. 19, pp. 3019-3025 (1991). Oxford University Press, Oxford, England.

Agrawal & Tang. "Site-specific functionalization of oligodeoxynucleotides for non-radioactive labelling." Tetrahedon Letters, vol. 31, pp. 1543-1546 (1990). Pergamon Press, Great Britain.

Sproat, et al. The synthesis of protected 5'-mercapto-2', 5'-dideoxyribonucleoside-3'-O-phosphoramidites; uses of 5'-mercapto-oligodeoxyribonucleotides. Nucleic Acids Research, vol. 15, pp. 4837-4848 (1987). IRL Press Limited, Oxford, England.

Nelson, et al. "Bifunctional oligonucleotide probes synthesized using a novel CPG support are able to detect single base pair mutations." Nucleic Acids Research, vol. 17, pp. 7187-7194 (1989). IRL Press Limited, Oxford, England.

Heid, et al. Real Time Quantitative PCR. Genome Research, vol. 6, pp. 986-994 (1996). Cold Spring Harbor Laboratory Press, Woodbury, New York.

Holland, et al. "Detection of specific polymerase chain reaction product by utilizing the 5' [to] 3' exonuclease activity of *Thermus aquaticus* DNA polymerase." Proceedings of the National Academy of Sciences, vol. 88, pp. 7276-7280 (1991). National Academy of Sciences, Washington, DC.

Lee, et al. "Allelic discrimination by nick-translation PCR with fluorogenic probes." Nucleic Acids Research, vol. 21, pp. 3761-3766 (1993). Oxford University Press, Oxford, England.

Nazarenko, et al. "A closed tube format for amplification and detection of DNA based on energy transfer." Nucleic Acids Research, vol. 25, pp. 2516-2521 (1997). Oxford University Press, Oxford, England.

Gibson, et al. "A Novel Method for Real Time Quantitative RT-PCR." Genome Research, vol. 6, pp. 995-1001 (1996). Cold Spring Harbor Laboratory Press, Woodbury, NY.

Tyagi & Kramer. "Molecular Beacons: Probes that Fluoresce upon Hybridization." Nature Biotechnology, vol. 14, pp. 303-308 (1996). Nature Publishing Group, New York.

Tyagi, et al. "Multicolor molecular beacons for allele discrimination." Nature Biotechnology, vol. 16, pp. 49-53 (1997). Nature Publishing Group, New York.

Whitcombe, et al. "Detection of PCR products using self-probing amplicons and fluorescence." Nature Biotechnology, vol. 17, pp. 804-807 (1999). Nature America, Inc., New York.

Van De Rijke, et al. "Up-converting phosphor reporters for nucleic acid microarrays." Nature Biotechnology, vol. 19, pp. 273-276 (2001). Nature Publishing Group, New York.

Corstjens, et al. "Infrared up-converting phosphors for bioassays." IEE Proceedings—Nanobiotechnology, vol. 152, pp. 64-72 (2005). Institution of Engineering and Technology, London.

Versalift, "Market Growth the evolution of the aserial lift industry," Oct. 1, 2002, Accessed on web Nov. 10, 2008.

Schultz et al., "Archived or directly swabbed latent fingerprints as a DNA source for STR typing." Forensic Science International, 127 (2002) 128-130.

Ibrahim et al., Complete nucleotde Sequence of the Cotton (*Gossypium barbadense* L.) Chloroplast Genome with a Comparative Analysis of sequence among 9 Dicot Plants. Genes and Genetic Systems vol. 81, pp. 311-321.

Hussein et al. "Molecular Characterization of Cotton Genotypes Using PCR-based Markers." Journal of Applied Sciences Research 3(10): 1156-1169 (2007).

Jiang et al., "Polyploid formation created unique avenues for response to selection in *Gossypium* (cotton)." Proceedings of the National Academy of Sciences, USA. vol. 95, pp. 4419-4424, Apr. 1998.

Lee et al., "The complete chloroplast genome sequence of *Gossypium hirsutum*: organization and phylogenetic relationships to other angiosperms." BMC Genomics 7:61, Mar. 2006.

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Unknown
<220> FEATURE:
<223> OTHER INFORMATION: primer  artificial sequence

<400> SEQUENCE: 1
cgccagggtt ttcccagtca cgac                                          24

<210> SEQ ID NO 2
<211> LENGTH: 17
<212> TYPE: DNA
<213> ORGANISM: Unknown
<220> FEATURE:
<223> OTHER INFORMATION: primer  artifical sequence

<400> SEQUENCE: 2
caggaaacag ctatgac                                                  17
```

SYSTEM AND METHOD FOR AUTHENTICATING SPORTS IDENTIFICATION GOODS

CROSS REFERENCE

This application is a continuation-in-part of patent application Ser. No. 11/437,265 having a filing date of May 19, 2006 that is related to provisional patent application 60/682,976 filed on May 20, 2005; this application is also a continuation-in-part of patent application Ser. No. 10/825,968 having a filing date of Apr. 15, 2004 that is related to provisional patent application 60/463,215 filed on Apr. 16, 2003; this application is also related to provisional patent application 60/874,425 having a filing date of Dec. 12, 2006; this application is also related to provisional patent application 60/877,875 having a filing date of Dec. 29, 2006; this application is also related to provisional patent application 60/877,869 having a filing date of Dec. 29, 2006; each of the patent applications being hereby incorporated by reference including co-pending patent application Ser. No. 11/954,009 now issued as U.S. Pat. No. 8,124,333; Ser. No. 11/954,030 now issued as U.S. Pat. No. 8,372,648; Ser. Nos. 11/954,038; 11/954,044 and 11/954,055; each of which were co-filed with the present application on Dec. 11, 2007.

FIELD

This invention relates to a system and method for authenticating sports identification garments as authentic. More particularly, the invention is related to a system and method for precisely verifying the authenticity of sports identification bibs.

BACKGROUND

With the dawn of modern technical advances comes the ability to duplicate, change, alter and distribute just about anything. The law enforcement organizations have called counterfeiting the crime of the $21^{st}$ century. Product counterfeiting is a serious and growing threat. Measures to defend against counterfeiters are being taken by many corporations, but they have not developed comprehensive, systematic, and cost-effective solutions to preventing counterfeiting.

Due to advancing counterfeiting techniques, traditional anti-counterfeit technologies are becoming obsolete. Additionally, governments and corporations that have invested a great deal of resources in fighting counterfeiting have experienced little success. Furthermore, law enforcement agencies that are burdened with efforts to combat violent crimes have insufficient resources to fight the "victimless" counterfeiting crime. For example, a company owning a famous brand name may have spent years developing and promoting the superior qualities of its goods to establish good will of the public and may be unable to stop a counterfeiter or a newcomer company product inferior quality goods.

Counterfeiting also extends to identification areas wherein identities, logos, and any other type of indicia may be faked. For example, in a competition, a competitor's racing number and other identification information such as name, sponsorship may be provided in the exterior of a garment such as a sporting bib. If a competitor's racing bib can be counterfeited, this may have serious consequences for the integrity of the sports, causing needless delays and aggravation to the organizers of sports events and sports promoters, as well as lost revenues if fake bibs cannot be detected by security guards or event employees who allow entrance access to a large number of participants in the event of a large competition such as the New York, Boston, or Chicago marathons.

Typically, information may be displayed on the exterior surfaces of garments in different ways, depending upon the nature of the information itself. Some information is permanently attached, such as the silk-screened name of the competitor. Other information, such as a manufacturer's label may be permanently affixed for advertising purposes. Other kinds of information, such as a competitor's racing bib displaying the competitor's number, is required to be attached only during the competition period. In practice, the most common way this is done is by temporarily attaching the racing bib to the garment with the use of safety pins.

Thus, there are no suitable or satisfactory approaches which have been proposed to prevent counterfeiting of sporting bibs if an individual decides to fake information and create a fake sporting bib. At best, manufacturers of racing bibs most often punch holes near the corners of the bibs in order to secure the bibs securely using safety pins, but this provides no defense against counterfeiting. Alternatively, other types of methods may decrease the probability of counterfeiting such as when the user wears the identification indicia which is part of the garment itself. However, even this approach has the disadvantage that counterfeiting of the garment might just as well occur very easily.

Therefore, no solutions appear to provide adequate ways to verify the authenticity of sporting garments and bibs which could stand against clever tampering, copying, spoofing, or other advanced counterfeiting techniques. With all these facts in mind, the realization of a simple method for labeling or printing sporting bibs using high quality anti-counterfeiting standards and a simple method for verification seems to be out of reach.

SUMMARY

This invention relates to methods for authenticating garments, particularly sport garments. The invention utilizes compositions which link biomolecules to visual or machine-detectable reporters. The methods of authentication comprise placing, associating, or integrating an optical reporter taggant with the garment or other textile item of interest. The optical reporters can be easily detected by using a high energy light source for excitation, with the location of labeled biomolecules identified by the presence of an optical reporter. The location and emission wavelength of the optical reporters provides a first level of security or authentication of the tagged item of interest. After the location of the optical reporters and associated biomolecules on the item has been determined, the biomolecules may be characterized and identified to further increase the level of security and/or authenticity of the item. When the biomolecule attached to the optical reporter is a DNA molecule, PCR or sequence analysis techniques can be utilized to further authenticate the item.

In one embodiment the invention provides an authentication method for authenticating a sports garment, the method comprising: applying a particular nucleic acid material associated with a particular sequence of nucleic acid bases to the garment; collecting a sample of the garment having the nucleic acid; and verifying whether the garment is genuine by detecting the particular nucleic acid material.

In some embodiments, the piece of garment to be authenticated may be selected from a group consisting of sport bibs, racing bibs, and removable sports identification patches.

The particular nucleic acid material may, in certain embodiments, be deoxy-ribo nucleic acid (DNA). In other embodiments the particular nucleic acid material may be ribonucleic acid (RNA).

In certain embodiments the method further comprises detecting the particular nucleic acid by performing a polymerase chain reaction (PCR) of the nucleic acid material.

In certain embodiments, the method may comprise applying the nucleic acid material to the garment comprises performing the marking throughout the entire surface of the garment. In other embodiments applying the nucleic acid material may comprise performing the marking in a specific area on the surface of the piece of garment. This specific marking may be in the form a indicia or a logo for the garment.

In certain embodiments, the method for authenticating a sports garment comprises the steps of, providing an optical reporter marker, the optical reporter marker having at least one light emitting upconverting phosphor particle linked to at least one nucleic acid material, the nucleic acid material having an identifiable portion, introducing the optical reporter marker to the garment of interest, then detecting the optical reporter marker associated with the garment with a light source, obtaining a sample of the optical reporter marker from the garment of interest for analysis; followed by analyzing the collected sample to detect the presence of the identifiable portion of the nucleic acid material linked to the upconverting phosphor particle.

This invention relates to methods for authenticating a sports garment that utilize compositions which link biomolecules to visual or machine-detectable reporters. The methods of authentication comprise placing, associating, or integrating an optical reporter taggant with the sports garment. The optical reporters can be easily detected by using a high energy light source for excitation, with the location of labeled biomolecules identified by the presence of an optical reporter. The location and emission wavelength of the optical reporters provides a first level of security or authentication of the tagged sports garment. After the location of the optical reporters and associated biomolecules on the article has been determined, the biomolecules may be characterized and identified to further increase the level of security and/or authenticity of the garment. When the biomolecule attached to the optical reporter is a DNA molecule, PCR or sequence analysis techniques can be utilized to further authenticate the sports garment.

In many embodiments of the method for authenticating a sports garment comprises the steps of;
  providing an optical reporter marker, the optical reporter marker having at least one light emitting upconverting phosphor particle linked to at least one nucleic acid taggant, the nucleic acid taggant having an identifiable portion,
  introducing the optical reporter marker to the sports garment,
  detecting the optical reporter marker associated with the sports garment with a light source,
  obtaining or collecting a sample of the optical reporter marker from the sports garment for analysis; and
  analyzing the collected sample to detect the presence of the identifiable portion of the nucleic acid taggant linked to the upconverting phosphor particle. In many embodiments the analyzing of the collected sample comprises determining the DNA sequence of the nucleic acid taggant, and comparing the determined DNA sequence with a known or reference DNA sequence.

In some embodiments, the optical reporter marker provided in the methods of the invention comprises a composition of the formula I:

$$(cOpR)\text{-}[L\text{-}(NA)]_m \qquad\qquad I$$

wherein: m is an integer greater than 1, (cOpR) is a coated optical reporter particle, (NA) is a nucleic acid oligomer of detectable sequence and L is a linking group covalently bound to the coated optical reporter particle and to the nucleic acid oligomer.

The (cOpR) of the composition may comprise an upconverting phosphor (UCP) material coated with silica. Where the compositions are coated with silica, the silica comprises at least one Si—O bond.

The (NA) of the composition maybe a single or double stranded DNA molecule having a length of between about 40 base pairs and about 1000 base pairs.

The linker L of the composition may comprise an alkylene moiety having a first end covalently bound to the coated optical reporter particle and a second end covalently bound to the nucleic acid oligomer.

Where the composition utilized in the methods of the invention comprises a (UCP), in certain embodiments, the (UCP) is an upconverting phosphor particle of the formula:

$$Y_x Yb_y Er_z O_2 S;\ \text{or}$$

$$Na(Y_x Yb_y Er_z)F_4;$$

wherein:
  x is from about 0.6 to about 0.95;
  y is from about 0.05 to about 0.35; and
  z is from about 0.1 to about 0.001.

In other embodiments, the linker L may be of the formula:

$$\text{-A-R}^1\text{—B—}$$

where $R^1$ is $C_{2\text{-}8}$alkylene, -A- is a group covalently bonded to the surface of the coated optical reporter and —B— is a group covalently bonded to the 3' or 5' end of the nucleic acid oligomer.

In other embodiments, a composition used in the methods for authenticating a sports garment of the invention has the formula:

$$(UCP)\text{-}[A\text{-}R^1\text{—}B\text{-}(DNA)]_m$$

where m is an integer greater than 1; UCP is an upconverting phosphor particle; DNA is a single or double stranded deoxyribonucleic acid oligomer; $R^1$ is $C_{2\text{-}8}$alkylene; -A- is a group capable of covalently bonding to the surface of the upconverting phosphor particle and —B— is a group capable of bonding to the 3' or 5' end of the deoxyribonucleic acid oligomer.

All patents and publications identified herein are incorporated herein by reference in their entirety.

DESCRIPTION

Figure 1:
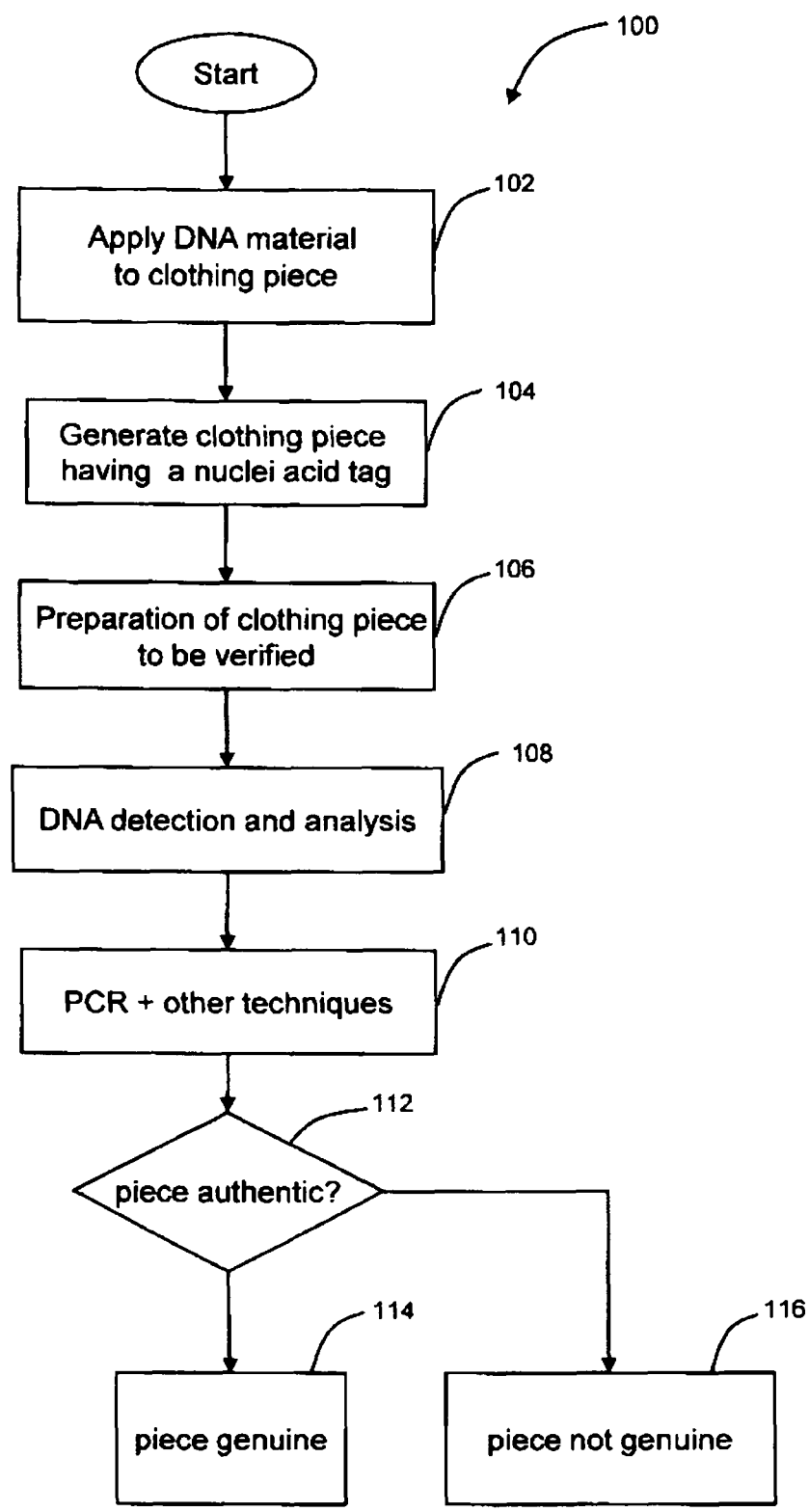
FIG. 1 is a flow chart of one embodiment of the methods of the invention.

Before the present methods for authenticating products are described, it is to be understood that this invention is not limited to particular product described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a taggant" includes a plurality of such taggants and reference to "the primer" includes reference to one or more primers and equivalents thereof known to those skilled in the art, and so forth.

If any publications are discussed here, they are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Although the description about the methods for verifying authenticity of a piece of clothing or garment contains many limitations in the specification, these should not be construed as limiting the scope of the claims but as merely providing illustrations of some of the presently preferred embodiments of this invention. Many other embodiments will be apparent to those of skill in the art upon reviewing the description. Thus, the scope of the invention should be determined by the appended claims, along with the full scope of equivalents to which such claims are entitled.

DEFINITIONS

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula —R'—R"—R"" where R' is alkylene, R" is —$SO_2$— and R"" is alkyl as defined herein.

"Amino" means a moiety of the formula —NR—R' wherein R and R' each independently is hydrogen or alkyl.

"Alkylsulfanyl" means a moiety of the formula —SR wherein R is alkyl as defined herein.

"Urea" or means a group of the formula —NR'—C(O)—NR"R"" wherein R', R" and R"" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —$SO_2$—NR'R" wherein R', R" and R"" each independently is hydrogen or alkyl.

"Optionally substituted", when used in association with "aryl", "phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —$SO_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

The term "emitting reporter" means a chemical substituent or material that produces, under appropriate excitation conditions, a detectable optical signal. The optical signal produced by an emitting reporter is typically electromagnetic radiation in the near-infrared, visible, or ultraviolet portions of the spectrum. The emitting reporters of the invention are generally up-converting reporters, but can also be for example, fluorescent and calorimetric substituents.

The term "phosphor particle" means a particle or composition comprising at least one type of upconverting phosphor material.

The term "primer" means a nucleotide with a specific nucleotide sequence which is sufficiently complimentary to a particular sequence of a target DNA molecule, such that the primer specifically hybridizes to the target DNA molecule.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide is amplified via a temperature cycling techniques in the presence of a nucleotide polymerase, preferably a DNA polymerase. This includes but is not limited to real-time PCR technology, reverse transcriptase-PCR, and standard PCR methods.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, e.g., can participate in hybridization reactions, i.e., cooperative interactions through Pi electrons stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" or "nucleotide" refer to single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like.

The term "linker" means a compound or a composition which covalently links a biomolecule to the surface of a coated emitting reporter. For example, but not limited to a silylated coated upconverting phosphor particle linked to a DNA molecule.

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

A "Nucleic acid tag" is a nucleic acid oligomer or fragment used to identify or authenticate a particular product. Nucleic acid tag and nucleic acid taggant are interchangeable throughout the specification.

The term "DNA taggant" means a nucleic acid tag which comprises deoxy nucleotides. A DNA taggant maybe double stranded or single stranded, cDNA, STR (short tandem repeats) and the like. The DNA taggant may also comprise modification to one or more nucleotides which aid in the identification or detection of the DNA taggant.

The term "DNA marker compound" means a marker compound utilized to identify or authenticate a particular product which comprises a specific DNA oligomer which is used to authenticate the particular product.

The term "garment", "piece of clothing", "piece of garment", "piece", "clothing", "bib" all refer to any type of material that may be used in conjunction with a uniform or clothing or accessory to be worn or used by an individual in order to provide proof of the individual's right to participate or benefit from a particular event.

The terms "those defined above" and "those defined herein" when referring to a variable incorporates by reference the broad definition of the variable as well as preferred, more preferred and most preferred definitions, if any.

Nomenclature and Structures

[76] In general, the nomenclature used in this application is based on AUTONOM™ v.4.0, a Beilstein Institute computerized system for the generation of IUPAC systematic nomenclature. Chemical structures shown herein were prepared using ISIS® version 2.5. Any open valency appearing on a carbon, oxygen sulfur or nitrogen atom in the structures herein indicates the presence of a hydrogen atom unless indicated otherwise. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure.

A method for labeling garments and readily verifying their authenticity as genuine by combining with a specified nucleic acid tag and then detecting the nucleic acid tag in the garment in an effective manner is described. FIG. 1 shows a flow chart of the general process 100 of introducing a nucleic acid tag/marker into or onto a piece of clothing and being able to detect the nucleic acid tag or marker incorporated therein. The process comprises applying at least one specific nucleic acid fragment as an authentication tag or marker for a product in step 102. The nucleic acid (NA) marker maybe DNA, cDNA, or other DNA material, or any other nucleic acid fragment comprising nucleic acids or nucleic acid derivatives. The marker may be a nucleic acid fragment that is single stranded or preferably, double stranded and may vary in length, depending on the product to be labeled as well as the detection technique utilized in the nucleic acid marker detection process.

The nucleic acid marker may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified to produce an acceptable nucleic acid marker(s). The length of the nucleic acid marker/tag usually ranges between about 100 to about 10 kilo bases, more usually about 500 bases to about 6 kb, and preferably about 1 kb to about 3 kb in length. In some embodiments, the form of the DNA may be linear or circular with sizes ranges from a few bases (5 bases) to genomic DNA (1M to 30 B bases).

There are several possible methods of DNA tagging such as: DNA may be combined with a dye for label or ID printing on the garment; a varnish for coating label or ID card; glue for label or ID card backing; other type of media for impregnation onto sports ID goods; or any combination thereof.

The nucleic acid taggant may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a nucleic acid marker may make detection of the marker easier and quicker, the use of a plurality of nucleic acid sequences such as STR and SNP, in general, give a higher degree of security against forgers.

For exemplary purposes, the nucleic acid concentration may vary from pico grams ($1\times10^{-12}$ gram) to micro grams ($1\times10^{-9}$ gram). In some embodiments, the DNA concentration may range from 1 ppb (parts per billion) to 500,000 ppm.

In certain embodiments for the methods of the invention, the nucleic acid marker is derived from DNA extracted from a specific plant source and rendered non-functional with scrambled sequences. The DNA may also be specifically digested and ligated to generate artificial nucleic acid sequences which are unique to the world. The digestion and ligation of the extracted DNA is completed by standard restriction digestion and ligase techniques known to those skilled in the art of molecular biology. Once the modified DNA taggant has been produced, the taggant is encapsulated into materials for protection against UV and degradation. The DNA encapsulant materials are generally of plant origin.

The marker compound maybe produced as a solid or liquid, water or oil based, a suspension, an aggregate and the like. An important feature of the marker compound are to protect the nucleic acid fragment from UV and other degradation factors that may degrade the nucleic acid taggant overtime, while the nucleic acid is acting as an authentication tag for a particular product. In certain embodiments, when the taggant is DNA, the nucleic acid tag may be encapsulated and suspended in a solvent solution (aqueous or organic solvent solution) producing a "stock" DNA taggant solution at a specified concentration. This stock DNA solution can then easily be added to the marker compound mixture at an appropriate concentration for the type of product to be authenticated. In certain instances, the DNA taggant maybe mixed with other components of the marker compound without any prior encapsulation. Several processes such as nucleic acid fragment encapsulation and other techniques utilized for protecting nucleotides, and in particular, DNA from degradation, are well known in the art.

In other embodiments, the marker compound mixture is to be able to camouflage or "hide" the specified nucleic acid tag with extraneous and nonspecific nucleic acid oligomers/fragments, thus making it difficult for unauthorized individuals, such as forgers to identify the sequence of the nucleic acid tag. In certain embodiments, the marker compound comprises a specified dsDNA taggant from a known source (i.e. mammal, invertebrate, plant and the like) along with genomic DNA from the corresponding or similar DNA source. The amount of the DNA taggant found in a marker compound varies depending on the particular product to be authenticated, the duration the taggant needs to be viable (e.g. 1 day, 1 month, 1 year, multiple years) prior to authentication, expected environmental exposure, the detection method to be utilized, etc.

After the nucleic acid fragment/marker compound with a known nucleic acid sequence has been manufactured or isolated, the method further comprises generating a piece of clothing having a DNA fragment as in step 104. The particular product or item generated may be tagged with a nucleic acid marker throughout the complete product or only in a predetermined region of the product. When the product to be authenticated is a solid, a specified amount of nucleic acid marker maybe incorporated throughout the volume of the product, only on the surface of the product or in some embodiments, placed only on a previously designated section of the product.

In many embodiments the item to be tagged initially is a textile thread or fabric in event 102, used for making the garment to be authenticated. The nucleic acid marker or taggant may be introduced to the thread or fabric at a desired concentration and intermixed with the dye(s) utilized in coloring the thread/fabric used in manufacturing the garment in event 104.

In other embodiments the item to be tagged or marked with the NA marker is a finished garment. In such embodiments the nucleic acid may be applied to the garment by various print transfer techniques, or by brushing, spraying, blotting or other method of applying paint or ink to a textile garment. Textiles may have a label with the manufactures name on it and may also be used as a region of the product which the nucleic acid marker is placed.

The particular product may be tagged with a nucleic acid marker throughout the complete piece or only in a predetermined region of the piece. In the case of a sport bib, the entire sport bib garment may have the nucleic acid tag incorporated completely throughout its entire surface. The above examples are presented for clarity and are not meant to be limiting in scope.

In general, when the taggant is dsDNA, PCR is the technique for taggant detection as described in event 110 below. The copy number of DNA taggant in a predetermined sample size of marker compound used for authentification is about 3 copies to about 100,000 copies, more usually about 10 copies to about 50,000 copies, and even more usually about 100 copies to about 10,000 copies of DNA taggant. The concentration of NA taggant incorporated within or on the garment may be varied as required depending upon particular embodiments of the invention. PCR can effectively detect extremely small amounts of DNA taggant and skilled persons can easily formulate DNA-labeled inks using the invention.

The embodiment of the method of authenticating and verifying an item depicted in FIG. 1 further comprises preparing the item to be verified as in step 106. In step 106, a sample may be collected of the particular item of interest for verification, i.e., DNA analysis on whether the item contains the nucleotide tag. For example, the preparation may comprise sampling the fabric or paint on the sports garment. The garment containing NA-tagged marker may be cut, scraped, abraded, or otherwise removed from the garment for analysis. Preparation of the Garment May Require Cleaning or Solvent Treatment Prior to removing a sample portion of the garment to be verified. Preparation of the item may occur without further purification, but usually, some extraction, isolation or purification of the nucleic acid tag obtained in the sample is required. Details on the extraction, concentration and purification techniques useful for the methods of the invention are described more fully below and also in the examples.

In certain embodiments the placement or position of the NA marker on the item of interest maybe located by the detection of materials or compounds configured to or associated with the NA fragment in the NA marker. Event 108 provides for such detection of the DNA marker. In many embodiments the DNA marker may be bound or coupled to, or otherwise associated with, a chemically or optically detectable label. Detection of DNA-labeled portions of the item may be carried out by optically detecting fluorescent dyes or upconverting phosphor particles which can be detected easily by UV and/or IR portable light sources. Thus, for example, a sports garment could be examined with a UV or IR light source to find a particular region or regions of the garment that contain a particular fluorescent marker. In this manner, only a small portion of the item (as identified by the fluorescent dye or particles) needs to be sampled for DNA. The materials or compounds utilized for locating the position of the NA marker on a garment or fabric of interest maybe coated with functional groups which can covalently bind to the NA fragment(s) of the NA marker, as described below. Event 108 may be carried out prior to event 106.

In general, analyzing the piece of clothing for the presence of DNA in event 110, comprises providing a "detection molecule" configured to the nucleic acid tag. A detection molecule includes but is not limited to a nucleic acid probe and/or primer set which is complementary to the sequence of the nucleic acid taggant, or a dye label or color producing molecule configured to bind and adhere to the nucleic acid taggant. When the detection of the nucleic acid taggant comprises amplifying the nucleic acid taggant using PCR, the detection molecule(s) are primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or quantitative authentication results. With the use of real time PCR, results from the analysis of the garment sample can be completed within 30 minutes to 2 hours, including extracting or purifying the nucleic acid taggant from the collected sample. Various embodiments utilize a wide range of detection methods besides for PCR and real time PCR, such as fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection.

The results of the analysis of the piece of clothing are reviewed to determine if the specific nucleic acid taggant was detected in the sample. If so, in step 112, the authentication of whether the piece of clothing is genuine or not can be verified. If the nucleic acid taggant is not found or detected in the piece of clothing of interest, the conclusion from the analysis is the that piece of clothing is not authentic or has been tampered with as in step 116. If the nucleic acid taggant is detected in the piece of clothing, then the piece of clothing is verified as being authentic as in step 114.

Thus, among the methods of detection for the NA marker on the garment, the NA marker may comprise an optical reporter material for quick detection of the position of the NA marker on the garment. For forensic DNA identification, DNA is extracted from DNA labeled objects and subjected to: PCR amplification with specific primers where amplicons are analyzed with either gel electrophoresis or capillary electrophoresis; RT-PCR amplification and detection may be used to obtain results within a very short period of time; or similar detection means.

In some embodiments, the quantity or concentration of the nucleic acid taggant within a collected sample can be determined and compared to the initial amount of nucleic acid taggant placed in the product to allow for the detection of fraud caused by diluting the product with inferior products by forgers. In general, quantitative detection methods comprise providing an internal or external control to evaluate the efficiency of detection from one sample/analysis to the next. The efficiency of detection may be affected by many parameters such as, probe hybridization conditions, molecules or substances in the product which may interfere with detection, and/or primer integrity, enzyme quality, temperature variations for detection methods utilizing PCR. By providing a control, in the detection methods, any variable conditions can be normalized to obtain an accurate final concentration of the nucleic acid tag in the product.

Incorporation of Functional Groups

In certain embodiments, the nucleic acid tag is labeled with at least one compound or "detection molecule" prior to being incorporated into the specified product to aid in the extraction and/or detection (see event 108 above) of the nucleic acid marker from the product after being placed in a supply chain. A detection molecule is a molecule or compound with at least one functionality. For example, fluorescent molecules, which may be in particulate form, may be configured to the nucleic acid marker for certain detection methods which are described in detail below.

In certain preferred aspects, suitable dyes include, but are not limited to, coumarin dyes, xanthene dyes, resorufins, cyanine dyes, difluoroboradiazaindacene dyes (BODIPY), ALEXA dyes, indoles, bimanes, isoindoles, dansyl dyes, naphthalimides, phthalimides, xanthenes, lanthanide dyes, rhodamines and fluoresceins. In other embodiments, certain visible and near IR dyes and IR materials are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the authentication process described herein. In certain embodiments, suitable dyes include, but are not limited to, fluorescein, 5-carboxyfluorescein (FAM), rhodamine, 5-(2'-aminoethyl)aminonaphthalene-1-sulfonic acid (EDANS), anthranilamide, coumarin, terbium chelate derivatives, Reactive Red 4, BODIPY dyes and cyanine dyes.

There are many linking moieties and methodologies for attaching fluorophore or visible dye moieties to nucleotides, as exemplified by the following references: Eckstein, editor, *Oligonucleotides and Analogues: A Practical Approach* (IRL Press, Oxford, 1991); Zuckerman et al., *Nucleic Acids Research*, 15: 5305-5321 (1987) (3' thiol group on oligonucleotide); Sharma et al., *Nucleic Acids Research*, 19: 3019 (1991) (3' sulfhydryl); Giusti et al., *PCR Methods and Applications*, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); AP3 Labeling Technology (U.S. Pat. Nos. 5,047,519 and 5,151,507, assigned to E.I. DuPont de Nemours & Co); Agrawal et al, *Tetrahedron Letters*, 31: 1543-1546 (1990) (attachment via phosphoramidate linkages); Sproat et al., *Nucleic Acids Research*, 15: 4837 (1987) (5' mercapto group); Nelson et al, *Nucleic Acids Research*, 17: 7187-7194 (1989) (3' amino group); and the like.

In other embodiments, a nucleic acid probe complementary to the nucleic acid marker is labeled with at least one compound or molecule with functionality to aid in the detection of the nucleic acid tag/marker. The techniques and dyes utilized in labeling the nucleic acid tag or the complementary probe are the same due to the nucleic acid nature of the tag and probe.

The detection molecules of the invention can be incorporated into probe motifs, such as Taqman probes (Held et al., Genome Res. 6: 986-994 (1996), Holland et al., Proc. Nat. Acad. Sci. USA 88: 7276-7280 (1991), Lee et al., Nucleic Acids Res. 21: 3761-3766 (1993)), molecular beacons; Tyagi et al., Nature Biotechnol., 16:49-53 (1998), U.S. Pat. No. 5,989,823, issued Nov. 23, 1999)) scorpion probes (Whitcomb et al., Nature Biotechnology 17: 804-807 (1999)), sunrise probes (Nazarenko et al., Nucleic Acids Res. 25: 2516-2521 (1997)), conformationally assisted probes (Cook, R., copending and commonly assigned U.S. Provisional Application No. 60/138,376, filed Jun. 9, 1999), peptide nucleic acid (PNA)-based light up probes (Kubista et al., WO 97/45539, December 1997), double-strand specific DNA dyes (Higuchi et al, Bio/Technology 10: 413-417 (1992), Wittwer et al, Bio/Techniques 22: 130-138 (1997)) and the like. These and other probe motifs with which the present detection molecules can be used are reviewed in Nonisotopic DNA Probe Techniques, Academic Press, Inc. 1992.

In other embodiments, the molecular beacon system is utilized to detect and quantify the nucleic acid tag from the product of interest. "Molecular beacons" are hairpin-shaped nucleic acid detection probes that undergo a conformational transition when they bind to their target that enables the molecular beacons to be detected. In general, the loop portion of a molecular beacon is a probe nucleic acid sequence which is complementary to the nucleic acid marker. The stem portion of the molecular beacon is formed by the annealing of arm sequences of the molecular beacon that are present on either side of the probe sequence. A functional group such as a fluorophore (e.g. coumarin, EDNAS, fluorescein, lucifer yellow, tetramethylrhodamine, texas red and the like) is covalently attached to the end of one arm and a quencher molecule such as a nonfluorescent quencher (e.g. DABCYL) is covalently attaches to the end of the other arm. When there is no target (nucleic acid tag) present, the stem of the molecular beacon keeps the functional group quenched due to its close proximity to the quencher molecule. However, when the molecular beacon binds to their specified target, a conformational change occurs to the molecular beacon such that the stem and loop structure cannot be formed, thus increasing the distance between the functional group and the quencher which enables the presence of the target to be detected. When the functional group is a fluorophore, the binding of the molecular beacon to the nucleic acid tag is detected by fluorescence spectroscopy.

In certain embodiments, a plurality of nucleic acid tags with varying sequences are used in labeling a particular product. The different nucleic acid tags can be detected quantitatively by a plurality of molecular beacons, each with a different colored fluorophore and with a unique probe sequence complementary to at least one of the plurality of nucleic acid tags. Being able to quantitate the various fluorphores (i.e. various nucleic acid tags) provides a higher level of authentication and security. It should be noted, that the other functional groups described above useful in labeling nucleic acid probes can also be utilized in molecular beacons for the present invention.

In other embodiments, the methods for authenticating an item, comprise labeling the item with an optical reporter marker linked to a nucleic acid tag, detecting the optical reporter, and then characterizing or verifying the nucleic acid taggant associated with the item in an effective manner, by nucleic acid sequencing, genotyping or like techniques. This embodiment allows for verification of tagged items in a manner that's helps prevent forgers counterfeit producers from substituting false or counterfeit goods in place of authentic items.

Figure 2:
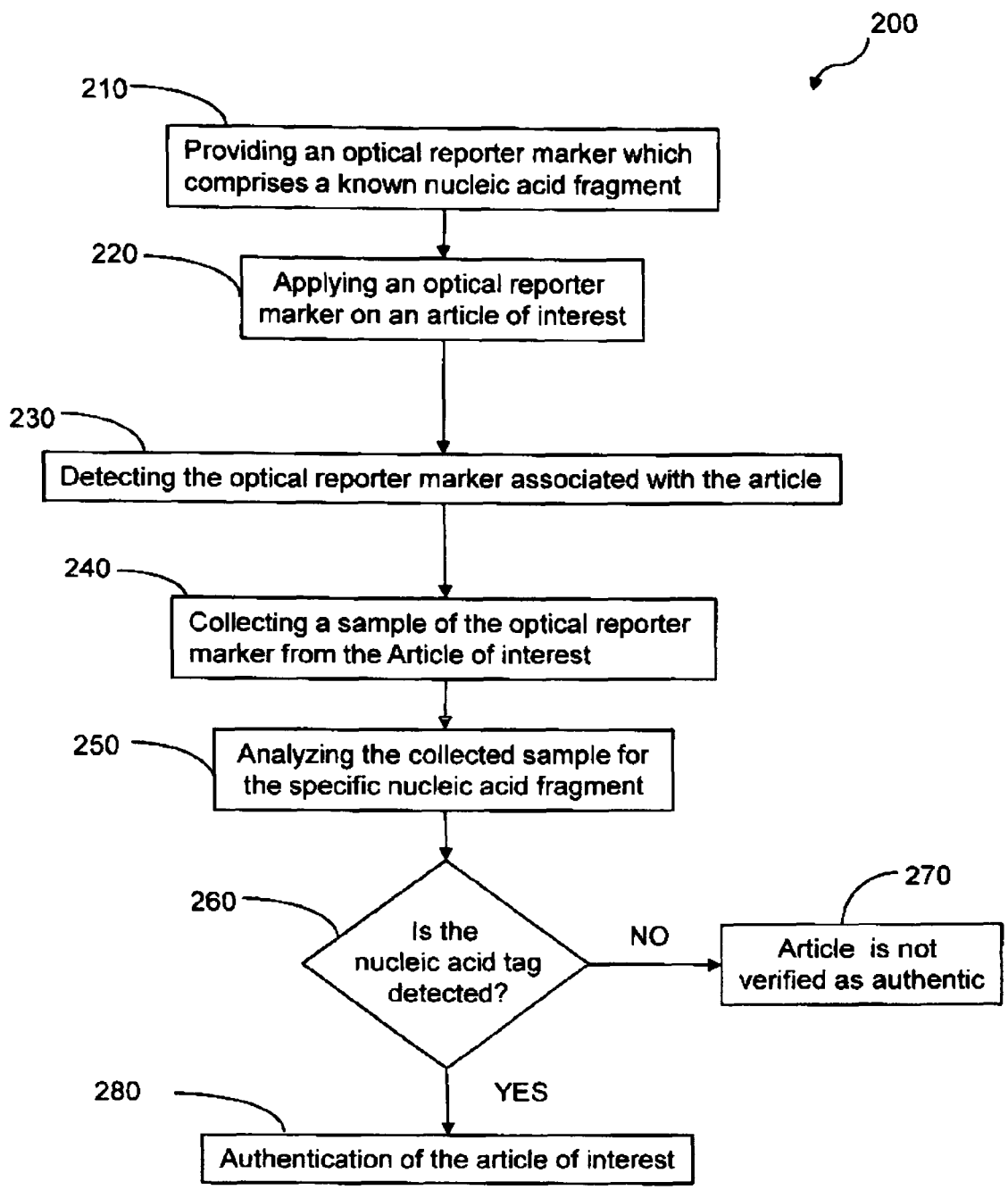
FIG. 2 is a flow chart of one embodiment of the methods for authenticating an item in accordance with the invention.

FIG. 2 is a flow chart illustrating generally a method 200 for authenticating an item with a nucleic acid-linked optical reporter marker in accordance with the invention. The method 200 comprises, at event 210, providing an optical reporter marker having a nucleic acid taggant linked to an optical reporter particle, the nucleic acid taggant having a known portion of its sequence identifiable or sequenceable.

The optical reporter particle of event 210 is a light emitting optical reporter and in most embodiments is an upconverting phosphor particle (UCP). In certain embodiments the upconverting phosphor particle UCP is coated with a silylation composition which is configured to covalently link to the nucleic acid taggant. Specific UCPs usable with the invention are described further below.

The nucleic acid (NA) taggant of event 210 may be DNA, cDNA, or any other nucleic acid fragment comprising nucleic acids or nucleic acid derivatives. The NA maybe a nucleic acid fragment that is single stranded or preferably double stranded and may vary in length, depending on the item to be labeled as well as the detection technique utilized in the nucleic acid detection process.

The nucleic acid marker may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified to produce an acceptable nucleic acid marker(s). The length of the nucleic acid tag usually ranges between about 50 to about 1 kilo bases, more usually about 100 bases to about 800 bases, and preferably 150 bases to about 500 b in length.

The nucleic acid taggant may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a nucleic acid marker may make detection of the marker easier and quicker, the use of a plurality of nucleic acid sequences such as STR and SNP, in general, give a higher degree of security against forgers.

In certain embodiments of the methods of the invention, the nucleic acid taggant is derived from DNA extracted from a specific plant source and is specifically digested and ligated to generate artificial nucleic acid sequences which are unique to the world. The digestion and ligation of the extracted DNA is completed by standard restriction digestion and ligase techniques known to those skilled in the art of molecular biology.

The optical reporter marker compound may be produced as a solid or liquid, water or oil based, a suspension, an aggregate or the like. The optical reporter marker allows for easy detection of where the optical reporter marker is located on or within the item of interest with basic high intensity light emitting equipment such as a hand-held ultraviolet (UV) lamp, IR emitting diode, hand-held IR laser and the like.

The optical reporter marker also enables the authentication of the item of interest by both confirming that the correct emission spectra/wavelength for the optical reporter particle is detected as well as being able to locate and determine by sequencing if the nucleic acid taggant comprises the correct nucleic acid sequence.

In certain embodiments, the optical reporter marker may camouflage or "hide" a specified nucleic acid tag of verifiable sequence by including extraneous and nonspecific nucleic acid oligomers/fragments, thus making it difficult for unauthorized individuals such as forgers to identify the sequence of the nucleic acid tag. In certain embodiments, the optical reporter marker comprises a specified dsDNA taggant from a known source (i.e. mammal, invertebrate, plant and the like) along with genomic DNA from the corresponding or similar DNA source. The amount of the DNA taggant found in a optical reporter marker compound may vary depending on the item to be authenticated, the duration or shelf-life the taggant needs to be viable (e.g. 1 day, 1 month, 1 year, multiple years) prior to authentication, expected environmental exposure, the detection method to be utilized, and other factors.

The method 200 for authenticating an item further comprises, in event 120, applying or introducing the nucleic acid-linked optical reporter marker to an item of interest in event. The nucleic acid-linked optical reporter marker may be applied in a specific, pre-determined amount or quantity. The item may be labeled with an optical reporter marker throughout the complete item, as a coating over the entire item, or only in a predetermined region or portion of the item. The marker may be applied in liquid solution, liquid dispersion, paste, powder, or other form. Application of the marker may be carried out using an eye-dropper, spoon, spatula, syringe, or other applicator tool. When the item to be authenticated is a solid, a specified amount of optical reporter marker maybe incorporated throughout the volume of the item, or only on the surface of the item or, in some embodiments, placed only on a previously designated section or portion of the item. In embodiments where the item to be authenticated is a fungible powder, the nucleic acid-lined optical reporter may be dispersed throughout the powdered material.

If the item is a textile or garment item, the marker could be either solid or liquid and applied to a predetermined area of the garment. Textiles may have a label with the manufactures name on it and may also be used as a region of the garment which the optical reporter marker is placed. The marker may be introduced, for example, by applying a liquid solution or suspension of the marker onto a selected portion of the garment and allowing the solution or suspension to dry by solvent evaporation to leave the markers in place. The marker can also be introduced by applying a binding solution containing DNA marker to the garment.

The authentication method 200 further comprises, in event 230, detecting the nucleic acid-linked optical reporter tag associated with the item of interest. Usually the detecting of the optical reporter marker associated with the item occurs after a period of time has lapsed. For example, after tagging the marked item may be introduced into a supply chain or the item may be placed into service. Frequently, forgers have the best access to items when they are being shipped from the manufacturer/producer to a retail outlet or location. Forgers also have access to the items of interest during maintenance or service of certain of products, such as aircraft, where the item of interest is inspected or replaced (i.e. fasteners). Having a method in which the producer can track and authenticate items or goods allows for a better monitoring of when and where counterfeit goods are being replaced with forgeries or otherwise being tampered with.

Detecting the optical reporter particle(s) represents a first level of authentication of the item. When the optical reporter particle is an upconverting phosphor particle, the marker can be detected by a high energy invisible light source such as an infrared laser, which may be hand-held and manipulated by a user, or suitably mounted to allow goods to be positioned in the lamp output. The infrared light is absorbed by the optical reporter particles, which in turn emit light at a wavelength that is characteristic of the optical reporter particle. Various upconverting phosphor compositions that provide selectable output wavelengths are known in the art, as described further below, and may be used with the invention. Once the optical reporter has been located within or on the item of interest, obtaining a sample of the optical reporter marker may occur at event 240.

In event 240, a sample is collected from the item of interest having the optical reporter marker. In certain embodiments, this may comprise visually inspecting the marker compound found in event 230, and/or scraping, cutting or dissolving a portion of the marked item to obtain a sample for analysis. When the item has entered a supply chain or has been in service, a manufacturer or an authorized individual can collect a sample of the optical reporter marker from the item at any desired point along the supply chain or during the service or routine maintenance of an item where the item is utilized for authentication purposes. The collecting of the sample may be carried out, for example, by wiping the item with a cloth (which may be moistened with solvent) to remove the marker from the item. The sample collecting in other embodiments may be achieved using a cutting, gouging, scraping, abrading, or other sampling tool configured to remove a portion of the item containing the optical reporter marker.

The embodiment of FIG. 2 further comprises analyzing the collected sample for the presence of the nucleic acid taggant in event 250. In many embodiments the analyzing of the collected sample comprises determining the DNA sequence of the nucleic acid taggant, and comparing the determined DNA sequence with a known or reference DNA sequence. The analysis of the sample collected from the item may occur without further purification, but in many embodiments some form of extraction, isolation or purification of the nucleic acid tag obtained in the sample may be required. Details on the extraction, concentration and purification techniques useful for the methods of the invention are described more fully below and also in the examples.

In general, analyzing the sample comprises providing a "detection molecule" configured to the nucleic acid tag. A detection molecule includes but is not limited to a nucleic acid probe and/or primer set which is complementary to at least a portion of the sequence of the nucleic acid taggant, or a dye label or color-producing molecule configured to bind and adhere to the nucleic acid taggant. The detection of the nucleic acid taggant may further comprise amplifying the nucleic acid taggant using PCR, with the detection molecule(s) being primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or fully quantitative authentication results. With the use of real time PCR, results from the analysis of the sample can be completed within 30 minutes to two hours, including extracting or purifying the nucleic acid taggant from the collected sample. Various embodiments of the invention may utilize a wide range of detection methods besides for PCR and real time PCR, such as DNA microarray, fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection. The method utilized to detect the nucleic acid is dependent on the quantity of nucleic acid taggant associated with the optical reporter marker. When only a few copies of NA taggant are collected in the marker sample, high sensitivity techniques such as PCR maybe preferable over fluorescent probes.

In event 260 the results of the analysis of the collected sample are reviewed and a query or determination is made as to whether or not the specific nucleic acid taggant was detected in the sample. If the nucleic acid taggant is not found or not detected in the collected sample of the item of interest at event 260, the conclusion at event 270 from the analysis is the that item is not authentic or has been tampered with. If the nucleic acid taggant is detected in the sample at event 260, then the item is verified in event 280 as being authentic.

If a determination is made in event 270 that an item is not authentic, a different, earlier point in the supply or commerce chain may be selected and events 230 through 260 may be repeated. Thus an item from an earlier point in the supply chain would be selected, the optical reporter marker detected, and a sample collected and analyzed. If it is again determined that the item is not authentic or has been otherwise tampered with, then events 230-260 may be repeated with an item selected from yet an earlier point in the supply chain. In this manner, the time and/or location of tampering or counterfeit substitute may be located.

In some embodiments, the quantity or concentration of the nucleic acid taggant within a collected sample can be determined and compared to the initial amount of nucleic acid taggant placed in the item to allow for the detection of fraud caused by diluting the item with inferior products by forgers. In general, such quantitative detection would further comprise, in event 250, providing an internal or external control to evaluate the efficiency of detection from one sample/analysis to the next. The efficiency of detection may be affected by many parameters such as, probe hybridization conditions, molecules or substances in the good which may interfere with detection, and/or primer integrity, enzyme quality, temperature variations for detection methods utilizing PCR. By providing a control, in the detection methods, any variable conditions can be normalized to obtain an accurate final concentration of the nucleic acid taggant in the item.

In certain embodiments a plurality of nucleic acid tags with varying sequences associated with a corresponding plurality of optical reporters may be used in labeling a single item. The different nucleic acid tags can be detected qualitatively by the plurality of optical reporters, each with a different emission wavelength linked to a unique sequenceable nucleic acid taggant.

Compounds Utilized in the Methods of the Invention

The methods of authentification of an item of the invention comprise compounds of the formula I:

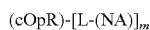

(cOpR)-[L-(NA)]$_m$ wherein:

m is an integer greater than 1;

(cOpR) is a coated optical reporter particle;

(NA) is a nucleic acid oligomer of detectable sequence; and

L is a linking group covalently bound to the coated optical reporter particle and to the nucleic acid oligomer.

While formula I specifically relates to linking nucleic acid oligomers or nucleotides to the surface of the coated optical reporter particle, it should be understood to the those skilled in the art that other biomolecules besides nucleotides can be covalently linked to L. Such biomolecules include but are not limited to peptides, proteins, antibodies, enzymes, DNA binding proteins and the like. These biomolecules, maybe modified to include lipids, carbohydrates, fluorescent and/or upconverting phosphor molecules or other detectable compounds or markers.

In many embodiments, NA is a DNA oligomer. The DNA oligomer maybe either single stranded DNA or double stranded DNA. In certain embodiments NA maybe comprise cDNA, RNA, STR (single tandem repeat) or SNP (single nucleotide polymorphism). NA oligomers of the compositions of the invention may also be modified to comprise at least one dUTP nucleic acid or at least one nucleic acid within the oligomer which has been modified to contain a detectable marker.

In many embodiments NA is a DNA oligomer having a length of between about 40 base pairs and about 1000 base pairs (per strand).

In other embodiments the DNA has a length of between about 80 and 500 base pairs (per strand).

In yet other embodiments the DNA has a length of between about 100 to about 250 base pairs (per strand).

The DNA used with the invention maybe natural or synthetically produced. All or a portion of the DNA may comprise an identifiable sequence.

In certain embodiments of formula I, the coated optical reporter comprises a visible or infrared detectable light emitting material selected from the group consisting of a fluorescent dye, an upconverting phosphor, a ceramic powder, or a quantum dot material. In most embodiments where the cOpR comprises a visible or infrared detectable light emitting material, the light emitting materials are excitable by UV, visible or an infrared light source.

In some embodiments, rare earth-doped ceramic particles are used as phosphor particles. Phosphor particles may be detected by any suitable method, including but not limited to up-converting phosphor technology (UPT), in which up-converting phosphors transfer lower energy infrared (IR) radiation into higher-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001);

Corstjens, et al., IEE Proc. Nanobiotechnol. 152(2):64 (2005), each incorporated by reference herein in its entirety.

In many embodiments, the phosphor nanoparticles utilized in the methods of the invention may be of the formula A $$(Y_xRE^1{}_yRE^2{}_z)_2O_3 \quad\quad A$$

wherein:
$RE^1$ and $RE^2$ each is a different rare earth element;
x is from about 0.6 to about 0.95;
y is from 0 to about 0.35; and
z is from 0.1 to about 0.001;
provided that y and z are not simultaneously equal to 0.

The rare earth elements $RE^1$ and $RE^2$ may each independently be selected from Ytterbium, Erbium, Holmium, Thulium, or Terbium.

In many embodiments $RE^1$ is Ytterbium.

In many embodiments $RE^2$ is Erbium.

The up-converting particles utilized in the methods of the invention may be spherical, non-agglomerated, non-porous particles with an average size of 40-60 nm. In general, particle sizes may range from about 10 nm to about 5 um in size. Such up-converting phosphor nanopowders such as doped yttrium oxide and yttrium oxysulfide are commercially available and may be obtained from such as Nanocerox, Inc., of Ann Arbor, Mich.

Suitable examples of up-converting phosphors are compounds of rare earths or elements from the group 111B such as: Na-yttrium fluoride, lanthanum fluoride, lanthanum oxysulphide, yttrium oxysulphide, yttrium fluoride, yttrium gallate, gadolinium fluoride, barium-yttrium fluorides, gadolinium oxysulphide as well as compounds of the above type doped with activator pairs such as ytterbium/erbium, ytterbium/thulium or ytterbium/holmium. Other suitable up-converting phosphors include chelate compounds of erbium, neodymium, thulium, holmium and praseodymium.

The following compositions are merely illustrative of some of the up-converting phosphor containing compositions that can be synthesized by the synthetic reaction schemes of the methods of the present invention. Various modifications to these synthetic reaction schemes can be made and will be suggested to one skilled in the art having referred to the disclosure contained in this application.

TABLE I

Upconverting Phosphor Compositions

| Phosphor Material | Absorber Ion | Emitter Ion |
|---|---|---|
| Oxysulfides ($O_2S$) | | |
| $Y_2O_2S$ | Ytterbium | Erbium |
| $Gd_2O_2S$ | Ytterbium | Erbium |
| $La_2O_2S$ | Ytterbium | Holmium |
| Oxyhalides ($OX_y$) | | |
| YOF | Ytterbium | Thulium |
| $Y_3OCl_7$ | Ytterbium | Terbium |
| Fluorides ($F_x$) | | |
| $YF_3$ | Ytterbium | |
| $GdF_3$ | Ytterbium | Erbium |
| $LaF_3$ | Ytterbium | Erbium |
| $NaYF_3$ | Ytterbium | Holmium |
| $BaYF_5$ | Ytterbium | Thulium |
| $BaY_2F_8$ | Ytterbium | Thulium |

TABLE I-continued

Upconverting Phosphor Compositions

| Phosphor Material | Absorber Ion | Emitter Ion |
|---|---|---|
| Gallates ($Ga_xO_y$) | | |
| $YGaO_3$ | Ytterbium | Erbium |
| $Y_3Ga_5O_{12}$ | Ytterbium | Erbium |
| Silicates ($Si_xO_y$) | | |
| $YSi_2O_5$ | Ytterbium | Holmium |
| $YSi_3O_7$ | Ytterbium | Thulium |

In certain embodiments the coated optical reporter used in the methods of the invention may also comprise at least one electromagnetic emitting material. An electromagnetic emitting material as part of the composition of the invention, allows for the composition to be detected by various methods and devices. Where the electromagnetic emitting material is detectable by mechanical devices which provide at least one source selected from the group consisting of an infrared radiation source, magnetic field source or electromagnetic pulse. This electromagnetic emitting material may be in conjunction with at least one light emitting material, such as an upconverting phosphor.

When the compositions used in the methods of authenticating an item of the invention comprise UCPs, the upconverting phosphor material/particle in certain embodiments have the formula B $$Y_xYb_yEr_zO_2S \quad\quad B$$

wherein:
x is from about 0.6 to about 0.95;
y is from about 0.05 to about 0.35; and
z is from about 0.1 to about 0.001.

In other embodiments, the upconverting phosphor particle may be of the formula C:

$$Na(Y_xYb_yEr_z)F_4 \quad\quad C$$

wherein
x is from about 0.6 to about 0.95
y is from about 0.05 to about 0.35; and
z is from about 0.1 to about 0.001.

In certain embodiments of formula I, L comprises an alkylene moiety having a first end covalently bound to the coated optical reporter particle (cOpR) and a second end covalently bound to the nucleic acid oligomer (NA).

In many embodiments of formula I, L is of the formula D:

$$-A-R^1-B- \quad\quad D$$

wherein:
$R^1$ is $C_{2-8}$alkylene;
-A- is a group covalently bonded to the surface of the coated optical reporter; and
—B— is a group covalently bonded to the 3' or 5' end of the nucleic acid oligomer.

In certain embodiments of formula D, —$R^1$— is —$(CH_2)_n$— and n is from 2 to 8.

In certain embodiments of formula D, —B— is:
—S—;
—O—;
—$NR^a$—;
—S—$(CH_2)_p$—;
—O—$(CH_2)_p$—;
—$NR^a$—$(CH_2)_p$—;
—S—$(CH_2)_q$—C(O)—$NR^a$—$(CH_2)_p$—;
—O—$(CH_2)_q$—C(O)—$NR^a$—$(CH_2)_p$—;

—NR$^a$—(CH$_2$)$_q$—C(O)—NR$^a$—(CH$_2$)$_p$—;
—S—C(O)—(CH$_2$)$_r$—C(O)—NR$^a$—(CH$_2$)$_p$—;
—O—C(O)—(CH$_2$)$_r$C(O)—NR$^a$(CH$_2$)$_p$—; or
—NR$^a$—C(O)—(CH$_2$)$_r$—C(O)—NR$^a$—(CH$_2$)$_p$—;
wherein:
p is from 2 to 8;
q is from 1 to 8;
r is from 2 to 8; and
each R$^a$ is independently hydrogen or a C$_{1-6}$-alkyl.
In certain embodiments of formula D, —B— is:
—S—(CH$_2$)$_q$—C(O)—NR$^a$—(CH$_2$)$_p$ or
—NR$^a$—C(O)—(CH$_2$)$_r$C(O)—NR$^a$—(CH$_2$)$_p$—;
wherein:
p is from 2 to 8;
q is from 1 to 8;
r is from 2 to 8; and
each R$^a$ is independently hydrogen or a C$_{1-6}$alkyl.
In other embodiments of formula D, —B— is:
—S—(CH$_2$)$_q$—C(O)—NR$^a$—(CH$_2$)$_p$ or
NR$^a$—C(O)—(CH$_2$)$_r$—C(O)—NR$^2$—(CH$_2$)$_p$—;
wherein:
p is from 2 to 6;
q is from 1 to 3; and
r is 2 or 3.
In other embodiments of formula D, —B— is
—S—CH$_2$—C(O)—NH—(CH$_2$)$_6$—
or
—NH—C(O)—(CH$_2$)$_3$—C(O)—NH—(CH$_2$)$_6$—.
In certain embodiments of formula D, -A- is —O—.

In many embodiments of formula I, the coated optical reporter (cOpR) is coated with silica. Usually when the coated optical reporter comprises a coating of silica, the silica comprises at least one Si—O bond.

The value of m in formula I will vary according to the surface area of the coated optical reporter and the number of functional groups on the optical reporter surface cable of bonding to -L-. The value of m is always greater than one, and usually greater than 10. Preferably m is greater than 100, and in many embodiments m is greater than 10$^3$. In many embodiments m may be, for example, between about 10 and about 10$^9$. In certain embodiments m may be from about 100 to about 10$^8$. In some embodiments m may be from about 10$^3$ to about 10$^7$.

In certain embodiments the compositions used in the methods of the invention are of the formula II:

(UCP)-[A-R$^1$—X—R$^2$—C(O)—NR$^a$—R$^3$-(DNA)]$_m$   II wherein:
m is an integer greater than 1;
UCP is an upconverting phosphor particle;
DNA is a single or double stranded deoxyribonucleic acid oligomer;
-A- is a group capable of covalently bonding to the surface of the Upconverting phosphor particle;
R$^1$ is C$_{2-8}$alkylene,
R$^2$ is C$_{1-8}$alkylene or —C(O)—C$_{1-8}$alkylene-;
—X— is —O—, —S— or —NR$^a$—;
R$^3$ is C$_{2-8}$alkylene; and
R$^a$ is hydrogen or C$_{1-6}$alkyl.
In certain embodiments of the invention, the subject composition may be of formula III:

(UCP)-[O—R$^1$—X—R$^2$—C(O)—NH—R$^3$-DNA]$_m$   III wherein m, R$^1$, R$^2$, R$^3$, UCP and DNA are as defined herein.

In certain embodiments of the invention, R$^1$ is C$_{2-6}$alkylene.
In certain embodiments of the invention, R$^2$ is C$_{1-6}$alkylene.
In certain embodiments of the invention, R$^3$ is C$_{2-6}$alkylene.
In certain embodiments of the invention, R$^2$ is —C(O)—C$_{2-6}$alkylene-.
In certain embodiments of the invention, R$^1$ is —(CH$_2$)$_s$— wherein s is from 2 to 6. In some embodiments s is 3.
In certain embodiments of the invention, R$^2$ is —(CH$_2$)$_t$— wherein t is from 1 to 6. In some embodiments t is 1.
In certain embodiments of the invention, R$^2$ is —C(O)—(CH$_2$)$_u$— wherein u is from 1 to 6. In some embodiments u is 2 or 3, preferably 2.
In certain embodiments of the invention, R$^3$ is —(CH$_2$)$_v$— wherein v is from 2 to 6. In some embodiments v is 6.
In certain embodiments of the invention, the subject composition may be of formula IV:

(UCP)-[O—(CH$_2$)$_s$—S—(CH$_2$)$_t$—C(O)—NH—(CH$_2$)$_v$-(DNA)]$_m$   IV wherein:
s is from 2 to 6;
v is from 2 to 6;
t is from 1 to 3; and
m, UCP and DNA are as defined herein.

In certain embodiments of the invention, the compositions may be of formula V:

(UCP)-[O—(CH$_2$)$_s$—NH—C(O)—(CH$_2$)$_u$—C(O)—NH—(CH$_2$)$_v$-(DNA)]$_m$   V wherein:
s is from 2 to 6;
v is from 2 to 6;
u is 2 or 3; and
m, UCP and DNA are as defined herein.

In certain embodiments of the invention, the compositions may be of formula VI:

(UCP)-[O—(CH$_2$)$_3$—S—CH$_2$—C(O)—NH—(CH$_2$)$_6$-(DNA)]$_m$   VI wherein m, UCP and DNA are as defined herein.

In certain embodiments of the invention, the compositions may be of formula VII:

(UCP)-[O—(CH$_2$)$_3$—NH—C(O)—(CH$_2$)$_3$—C(O)—NH—(CH$_2$)$_6$-(DNA)]$_m$   VII wherein m, UCP and DNA are as defined herein.

Encapsulation of a Nucleic Acid Tag

In some embodiments, the nucleic acid marker is incorporated into the product in the presence of molecules which encapsulate the nucleic acid marker by forming microspheres. Encapsulating the nucleic acid marker has the benefit of preventing the nucleic acid marker from degrading while present in a supply chain or during the use of the marked product. The encapsulating materials in most embodiments are of plant origin but may also be synthetically produced materials. The encapsulation of a nucleic acid tag comprises placing the nucleic acid tag into a solvent with a polymer configured to form a microsphere around the tag. The polymers used can be selected from biodegradable or non-biodegradable polymers. Preferred biodegradable polymers are those such as lactic and glycolic acids and esters such as polyanhydrides, polyurethanes, butyric polyacid, valeric polyacid, and the like. Non biodegradable polymers appropriate for encapsulation are vinyletylenene acetate and acrylic polyacid, polyamides and copolymers as a mixture thereof. The polymers can also be selected from natural compounds such as dextran, cellulose, collagen, albumin, casein and the like.

Certain aspects of the invention comprise labeling the microspheres to benefit in the capture of the nucleic acid tag during the extraction of the label from the product of interest. The microspheres may comprise magnetically charged molecules which allow the microspheres containing the nucleic acid tag to be pulled out of a solution by a magnet.

The microspheres can also be labeled with streptavidin, avidin, biotinylated compounds and the like. Labeling the microspheres aids in the purification of the nucleic acid tag prior to detection and also is useful in concentrating the nucleic acid tag so as to enable in some embodiments, the nucleic acid tag to be detected without PCR amplification.

In other embodiments, the nucleic acid marker is applied or added to the product without being encapsulated in microspheres. For example, the nucleic acid marker may be dissolved in a solution compatible with the composition of the particular product such as a textile and then the solution comprising the nucleic acid marker is placed on the surface of the textile product, allowing the nucleic acid marker to be absorbed into the fabric.

Incorporation of the Nucleic Acid Tag into the Particular Piece of Clothing or Textile The method of incorporating the nucleic acid tag into a piece of garment or clothing depends significantly on the type of piece of clothing to be authenticated as described above. The nucleic acid tag maybe added to a marker compound in a "naked" or encapsulated form at a predetermine concentration which allows for accurate detection of the nucleic acid taggant. The marker compound is generally a liquid but in certain embodiments may be a solid. The marker compound maybe a liquid and after the addition of the nucleic acid taggant, is dried prior to introducing the marker as an inert substance. When the marker compound comprising a nucleic acid taggant is in liquid form, the marker compound is generally applied to the product in a lacquer, paint or liquid aerosol form.

In other embodiments the nucleic acid taggant may be applied to the finished garment as a paint/ink on a predesignated position on the garment. The mixture utilized is formulated to allow detection of an up converting phosphor particle, with minimal quenching of the light emission from the UCP when excited by the appropriate light source.

When the item is a finished garment, for example, the nucleic acid taggant can be mixed with paints appropriate for the type fabric that the garment being marked is made from. The NA taggant is added to the dye or paint mixture at an appropriate concentration to allow for adequate detection of the NA marker. If the NA taggant marker comprises an UCP composition, the paint mixture is compatible with the NA taggant as to not quench the emission of the UCP particle. In some instances, the NA taggant marker may be introduced to the item during silk screening, applying an appliqué or while applying a waterproof solution to the garment.

Nucleic Acid Tag Extraction and Capture Methods

A variety of nucleic acid extraction solutions have been developed over the years for extracting nucleic acid sequences from a sample of interest. See, for example, Sambrook et al. (Eds.) Molecular Cloning, (1989) Cold Spring Harbor Press. Many such methods typically require one or more steps of, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

In some embodiments, the authentication process comprises capturing the nucleic acid tag directly with a complementary hybridization probe attached to a solid support. In general, the methods for capturing the nucleic acid tag involve a material in a solid-phase interacting with reagents in the liquid phase. In certain aspects, the nucleic acid probe is attached to the solid phase. The nucleic acid probe can be in the solid phase such as immobilized on a solid support, through any one of a variety of well-known covalent linkages or non-covalent interactions. In certain aspects, the support is comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxyethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of capturing the nucleic acid tag, a nucleic acid probe can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin are useful. Examples of other functional group linkers include ester, amide, carbamate, urea, sulfonate, ether, and thioester. A 5' or 3' biotinylated nucleotide can be immobilized on avidin or streptavidin bound to a support such as glass.

Depending on the initial concentration of the nucleic acid tag added to the product of interest, the tag can be detected quantitatively without being amplified by PCR. In some embodiments, a single stranded DNA tag labeled with a detection molecule (i.e. fluorophore, biotin, etc.) can be hybridized to a complementary probe attached to a solid support to allow for the specific detection of the "detection molecule" configured to the tag. The nucleic acid DNA tag can also be double stranded, with at least one strand being labeled with a detection molecule. With a dsDNA tag, the nucleic acid tag must be heated sufficiently and then quick cooled to produce single stranded DNA, where at least one of the strands configured with a detection molecule is capable of hybridizing to the complementary DNA probe under appropriate hybridization conditions.

In certain aspects of the invention, the complementary probe is labeled with a detection molecule and allowed to hybridize to a strand of the nucleic acid tag. The hybridization of the probe can be completed within the garment or can be completed after the nucleic acid tag/marker has been extracted from the product. The direct detection methods described herein depend on having a large initial concentration of nucleic acid label embedded into the pieces of clothing or rigorous extraction/capture methods which concentrate the nucleic acid tag extracted from a large volume or mass of a particular product.

In one embodiment, where the NA taggant comprises an up converting particle, the extraction of the NA taggant marker varies depending on the garment being authenticated. When the NA marker comprises a UCP particle, the NA marker can be located by detecting the presence of the UCP by an appropriate light source. The NA marker can then be extracted from the garment by scraping, cutting out, or dissolving the portion of the garment which is determined to have the presence of the correct up-converting phosphor particle(s). Once the portion of the item containing the NA marker has been removed the item of interest, the NA marker may isolated and/or prepared for PCR analysis utilizing techniques known to those skilled in the art of PCR sample preparation.

Real-Time PCR Amplification

In many embodiments, the authentication process comprises amplifying the nucleic tag by polymerase chain reaction. However, conventional PCR amplification is not a quantitative detection method. During amplification, primer dimers and other extraneous nucleic acids are amplified together with the nucleic acid corresponding to the analyte. These impurities must be separated, usually with gel separation techniques, from the amplified product resulting in possible losses of material. Although methods are known in which the PCR product is measured in the log phase, these methods require that each sample have equal input amounts of nucleic acid and that each sample amplifies with identical efficiency, and are therefore, not suitable for routine sample analyses. To allow an amount of PCR product to form which is sufficient for later analysis and to avoid the difficulties noted above, quantitative competitive PCR amplification uses an internal control competitor and is stopped only after the log phase of product formation has been completed.

In a further development of PCR technology, real time quantitative PCR has been applied to nucleic acid analytes or templates. In this method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time. Reverse transcriptase (RT)-real time PCR (RT-PCR) has also been described (Gibson et al., 1996). Numerous commercially thermal cyclers are available that can monitor fluorescent spectra of multiple samples continuously in the PCR reaction, therefore the accumulation of PCR product can be monitored in 'real time' without the risk of amplicon contamination of the laboratory. Heid, C. A.; Stevens, J.; Livak, K. L.; Williams, P. W. (1996). Real time quantitative PCR. Gen. Meth. 6: 986-994.

In some embodiments of the anti-counterfeit authentication process, real time PCR detection strategies may be used, including known techniques such as intercalating dyes (ethidium bromide) and other double stranded DNA binding dyes used for detection (e.g. SYBR green, a highly sensitive fluorescent stain, FMC Bioproducts), dual fluorescent probes (Wittwer, C. et al., (1997) BioTechniques 22: 176-181) and panhandle fluorescent probes (i.e. molecular beacons; Tyagi S., and Kramer FR. (1996) Nature Biotechnology 14: 303-308). Although intercalating dyes and double stranded DNA binding dyes permit quantitation of PCR product accumulation in real time applications, they suffer from the previously mentioned lack of specificity, detecting primer dimer and any non-specific amplification product. Careful sample preparation and handling, as well as careful primer design, using known techniques must be practiced to minimize the presence of matrix and contaminant DNA and to prevent primer dimer formation. Appropriate PCR instrument analysis software and melting temperature analysis permit a means to extract specificity and may be used with these embodiments.

PCR amplification is performed in the presence of a non-primer detectable probe which specifically binds the PCR amplification product, i.e., the amplified detector DNA moiety. PCR primers are designed according to known criteria and PCR may be conducted in commercially available instruments. The probe is preferably a DNA oligonucleotide specifically designed to bind to the amplified detector molecule. The probe preferably has a 5' reporter dye and a downstream 3' quencher dye covalently bonded to the probe which allow fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan® PCR system from Perkin-Elmer, which allows real time PCR detection.

In an alternative embodiment, the reporter dye and quencher dye may be located on two separate probes which hybridize to the amplified PCR detector molecule in adjacent locations sufficiently close to allow the quencher dye to quench the fluorescence signal of the reporter dye. As with the detection system described above, the 5'-3' nuclease activity of the polymerase cleaves the one dye from the probe containing it, separating the reporter dye from the quencher dye located on the adjacent probe preventing quenching of the reporter dye. As in the embodiment described above, detection of the PCR product is by measurement of the increase in fluorescence of the reporter dye.

Molecular beacons systems are frequently used with real time PCR for specifically detecting the nucleic acid template in the sample quantitatively. For instance, the Roche Light Cycler™ or other such instruments may be used for this purpose. The detection molecule configured to the molecular beacon probe may be visible under daylight or conventional lighting and/or may be fluorescent. It should also be noted that the detection molecule may be an emitter of radiation, such as a characteristic isotope.

The ability to rapidly and accurately detect and quantify biologically relevant molecules with high sensitivity is a central issue for medical technology, national security, public safety, and civilian and military medical diagnostics. Many of the currently used approaches, including enzyme linked immunosorbant assays (ELISAs) and PCR are highly sensitive. However, the need for PCR amplification makes a detection method more complex, costly and time-consuming. In certain embodiments anti-counterfeit nucleic acid tags are detected by Surface Enhanced Raman Scattering (SERS) as described in U.S. Pat. No. 6,127,120 by Graham et al. SERS is a detection method which is sensitive to relatively low target (nucleic acid) concentrations, which can preferably be carried out directly on an unamplified samples. Nucleic acid tags and/or nucleic acid probes can be labeled or modified to achieve changes in SERS of the nucleic acid tag when the probe is hybridized to the nucleic acid tag. The use of SERS for quantitatively detecting a nucleic acid provides a relatively fast method of analyzing and authenticating a particular product.

Another detection method useful in the invention is the Quencher-Tether-Ligand (QTL) system for a fluorescent biosensor described in U.S. Pat. No. 6,743,640 by Whitten et al. The QTL system provides a simple, rapid and highly-sensitive detection of biological molecules with structural specificity. QTL system provides a chemical moiety formed of a quencher (Q), a tethering element (T), and a ligand (L). The system is able to detect target biological agents in a sample by observing fluorescent changes.

The QTL system can rapidly and accurately detect and quantify target biological molecules in a sample. Suitable examples of ligands that can be used in the polymer-QTL approach include chemical ligands, hormones, antibodies, antibody fragments, oligonucleotides, antigens, polypeptides, glycolipids, proteins, protein fragments, enzymes, peptide nucleic acids and polysaccharides. Examples of quenchers for use in the QTL molecule include methyl viologen, quinones, metal complexes, fluorescent dyes, and electron accepting, electron donating and energy accepting moieties. The tethering element can be, for example, a single bond, a single divalent atom, a divalent chemical moiety, and a multivalent chemical moiety. However, these examples of the ligands, tethering elements, and quenchers that form the QTL molecule are not to be construed as limiting, as other suitable examples would be easily determined by one of skill in the art.

Kits for Authenticating Items Using Nucleic Acid-Linked Optical Reporters

The invention also provides kits for authenticating items of interest using the methods of the invention. The kits of the invention may comprise, for example, a container of the optical reporter marker, and a sample tube for holding a collected sample of the item or item to be authenticated. The kits may further comprise an applicator for applying a sample of the optical reporter to the item. The kits may still further comprise a collection tool for taking a sample of the labeled item for transfer to the sample tube. The kits may further comprise a portable light source for detecting the optical reporters.

By way of example, the optical reporter marker may be in the form of a liquid solution or dispersion, and the container with the kit would be suitably configured for holding a liquid. The applicator of the kit may comprise an "eye-dropper" for applying liquid optical reporter marker solution to the item in droplet form, a spatula for smearing the solution on an item, a syringe for injecting the solution into an item, or like type of applicator. The collection tool of the kit may comprise a spoon, gouge, a scraping or abrading tool for removing a sample of the labeled item, a blade or scissors for cutting a piece of the item, a cloth (which may be solvent-moistened) for wiping a sample from the item, or the like. The sample tube of the kit may comprise a sealable vial or eppendorf tube, and may contain solvent or solution for extraction of the optical reporter marker from the sample taken from the tagged item. The portable light source of the kit may comprise a hand-held UV lamp suitable for detecting the optical reporter marker.

The kit may further comprise primers and/or probes as well as solutions appropriate for PCR analysis. The kit may further comprise a small PCR instrument for analysis of the extracted optical reporter marker.

The kits of the invention thus provide a convenient, portable system for practicing the methods of the invention.

Synthesis of UCP Particles Covalently Linked to Biomolecules

Nucleotide-labeled optical reporters in accordance with the invention can be made by a variety of methods, including those depicted in the co-pending U.S. application "Methods for linking Optical Reporters to Biomolecules," which is hereby incorporated by reference.

Preferred methods for preparing UCP particles covalently linked to DNA are provided in the following Examples.

EXAMPLES

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Identification Materials

Forgery of sports identification materials could pose a serious setback to the integrity of sporting events as well as compromising the position of honest competitors and creating a major financial stress for event promoters and sponsors. Creating genuine sports ID garments with embedded nucleic acid material would be extremely advantageous provided that verification methods may be performed within a reasonable amount of time. As mentioned previously, for example, the nucleic acid material may be combined with: a printing ink for label or ID printing; a varnish for coating label may be applied; glue for labeling or ID card backing; other type of media for impregnation onto identification cards may be used; or any combination thereof.

The method of detection would have to be expeditious for the best effect. For forensic DNA identification, DNA would be extracted from DNA labeled objects and subjected to: PCR amplification with specific primers where amplicons will be analyzed with either gel electrophoresis or capillary electrophoresis; RT-PCR amplification and detection may be used to obtain results within an hour; or similar detection means.

Figure 3:
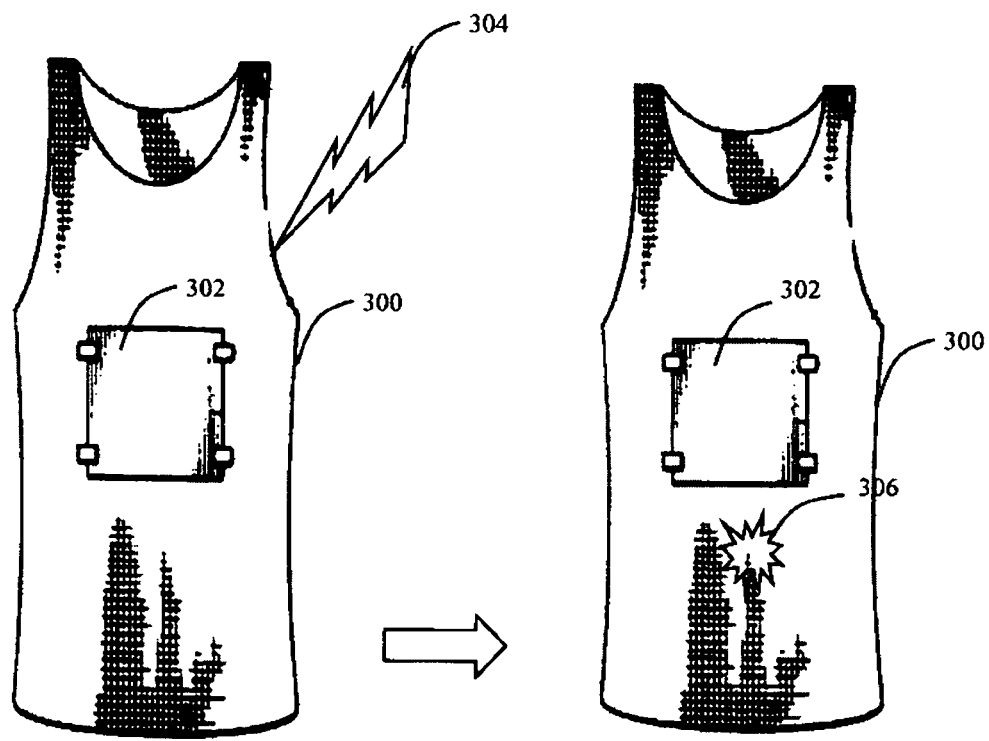
FIG. 3 is an illustrative diagram of a labeling process of a sporting garment with informational indicia in accordance with one of the embodiments of the present invention.

Referring to FIG. 3, a sports shirt 300 is illustrated with a sport's indicia garment section or patch 302 affixed in the front of the shirt 300 with either safety pins or glued to the shirt 300. Of course, the shirt 300 may also contain athletic team insignias and logos. Generally, the insignias and logos are provided on the back or the front of the shirt, and sometimes on both. The shirt 300 and specially the patch 302 is labeled with the DNA as shown by an arrow 304 in a DNA labeling process. The resulting shirt 300 now contains the DNA tagging 306 which authenticates the sport identification or patch 302 as authentic.

Figure 4:
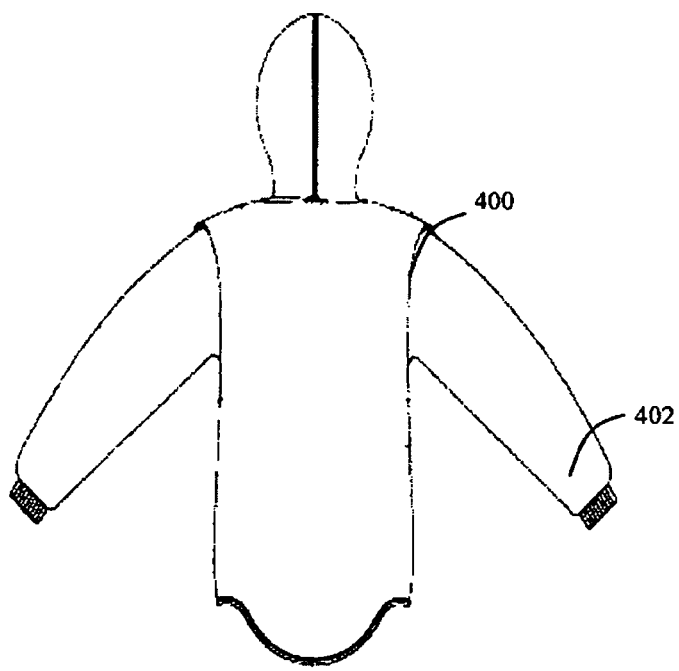
FIG. 4 is an illustrative diagram of a garment sporting bib according to one of the embodiments of the present invention.

Referring to FIG. 4, an alternative embodiment of a sports identification garment is shown. A sports bib 400 is shown worn over a shirt 402. This may or may not be necessary depending on the sports competition. Usually, athletes such as marathon runners compete and run with a thin undershirt and a sport bib identification which contains various information insignia thereon. The process for labeling sports bib 400 is identical to the one applied for the patch 302 and shirt 300.

One may note that the present invention is a remarkable improvement over any previous means of preventing forgery of sports identification bibs or garments.

Example 2

Up-converting phosphor nanopowder (doped yttrium oxide and yttrium oxysulfide upconverting particles) were obtained from Nanocerox, Inc., Ann Arbor, Mich.

| ABBREVIATIONS | |
|---|---|
| UCP | Up converting phosphor |
| UTP | Up converting phosphor technology |

| ABBREVIATIONS | |
|---|---|
| OpR | optical reporter particle |
| cOpR | coated optical reporter particle |
| TEOS | tetraethoxysilane, tetraethyl orthosilicate; ethyl silicate; silicic acid, tetraethyl ester; or silicon ethoxide |
| MOS | methyl oxysilane |
| EOS | ethyl oxysilane |
| POS | propyl oxysiline |
| NHS | N-Hydroxsuccinimde |
| IOA | Iodoacetamide |
| DIPCI | Diisopropylcarbodiimide |
| DCM | dichloromethane/methylene chloride |
| DIPEA | diisopropyl ethylamine |
| DMF | N,N-dimethylformamide |
| DMAP | 4-dimethylaminopyridine |
| ECDI | 1-ethyl-3-(3'-dimethylaminopropyl)carbodiimide |
| EtOAc | ethyl acetate |
| EtOH | ethanol |
| hplc | high performance liquid chromatography |
| mCPBA | m-chloroperbenzoic acid |
| MeCN | acetonitrile |
| TLC | thin layer chromatography |

Doped Yttrium Oxysulfide with Oxypropylsulfanylacetamide-Linked DNA

The synthetic procedure of this Example is shown below in Scheme A.

SCHEME A

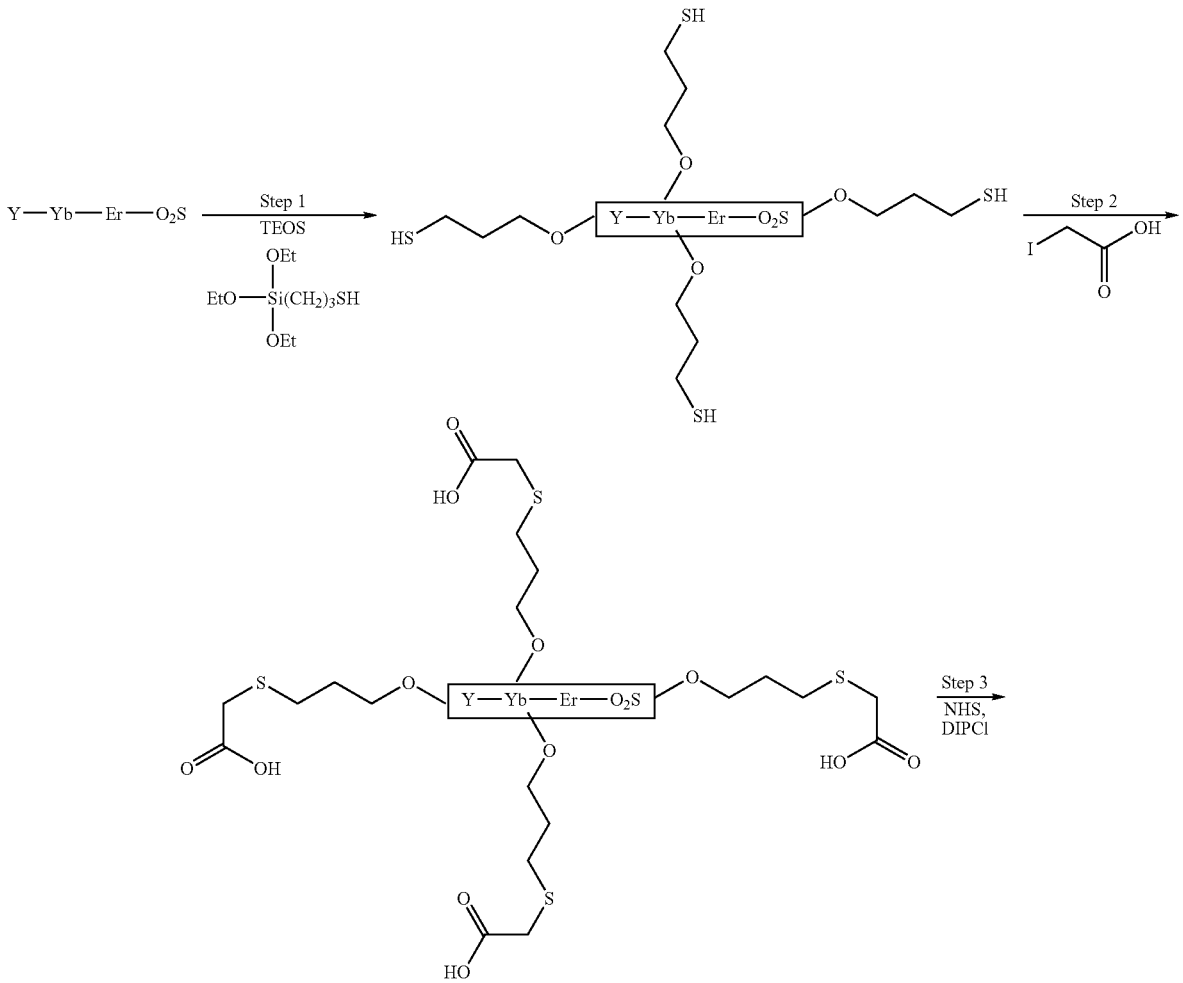

-continued

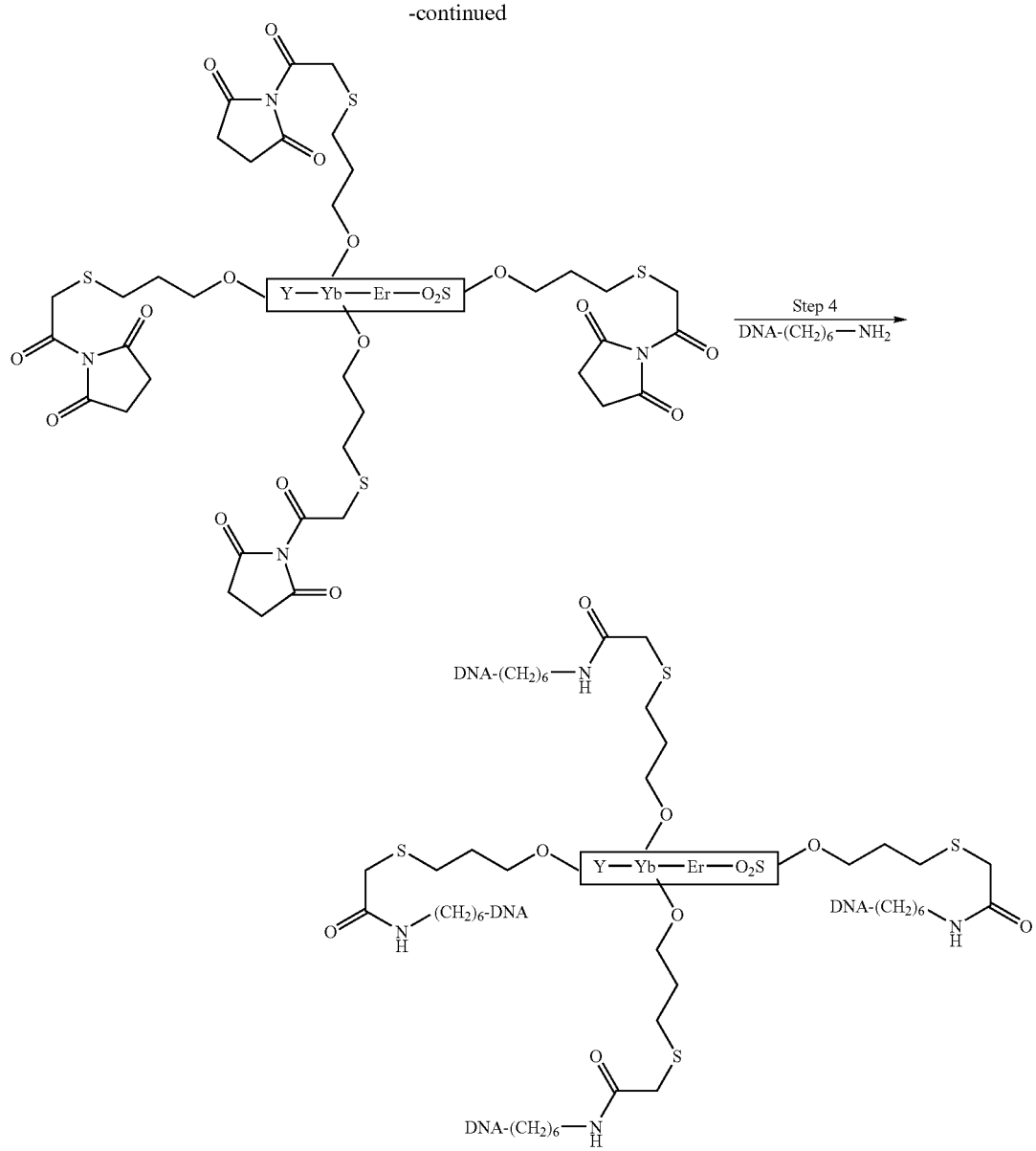

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide up converting particles as well as an amine linked DNA oligomer.

Detection of Bound DNA to Phosphor Particles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Tag mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One pre-heating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted 1/10, 1/100, and 1/1000, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

The results from the RT-PCR experiment where similar to those shown in FIG. 5, discussed below in Example 3.

Example 3
Doped Yttrium Oxysulfide with (oxy-propylamino)-acetic acid 5-amino-4-oxo-pentyl ester-linked DNA
The synthetic procedure of this example is shown below in Scheme B.
SCHEME B
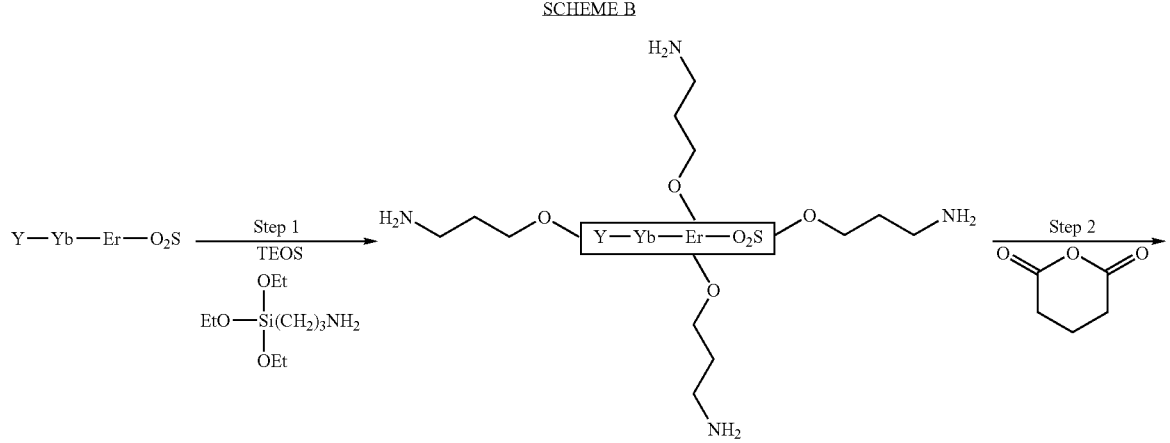
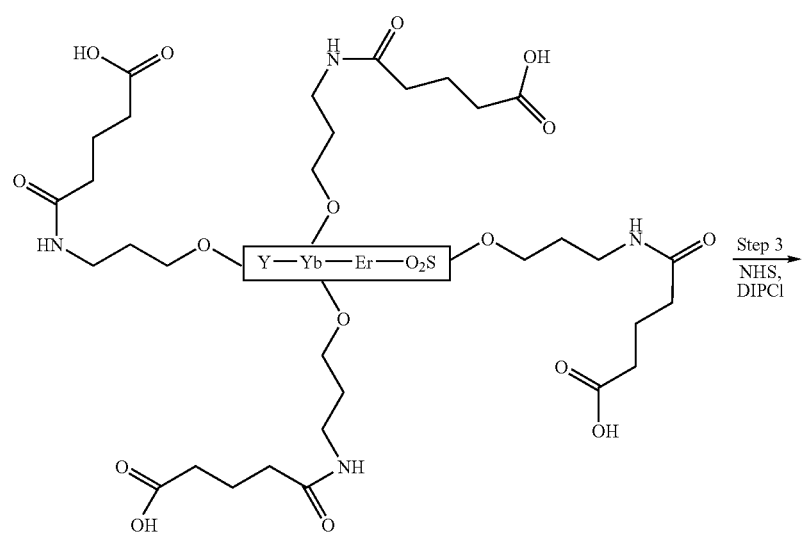

-continued

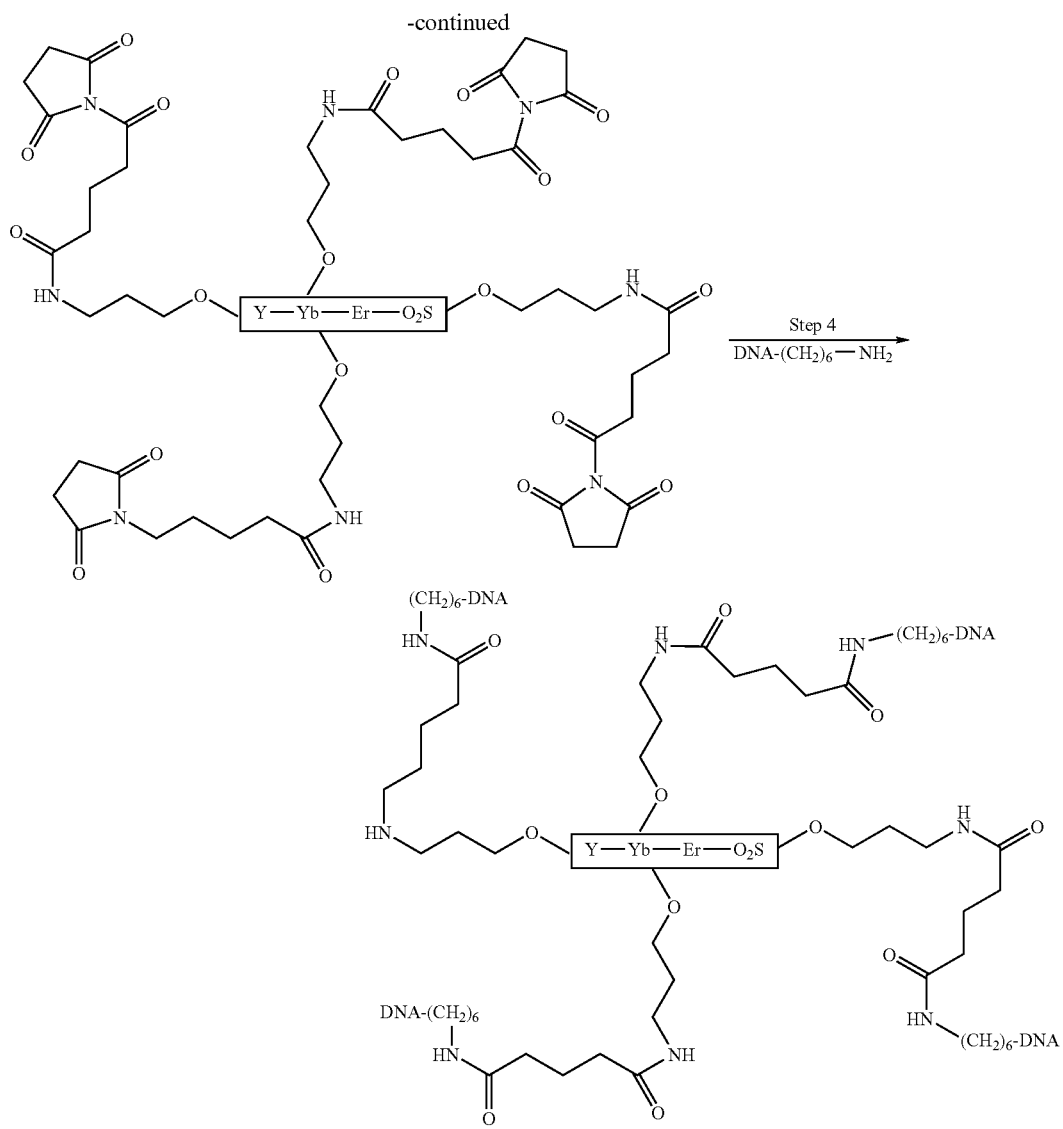

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide up converting particles as well as an amine linked DNA oligomer.
Detection of Bound DNA to Phosphor Particles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Taq mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One preheating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted 1/10, 1/100, and 1/1000, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

Figure 5:
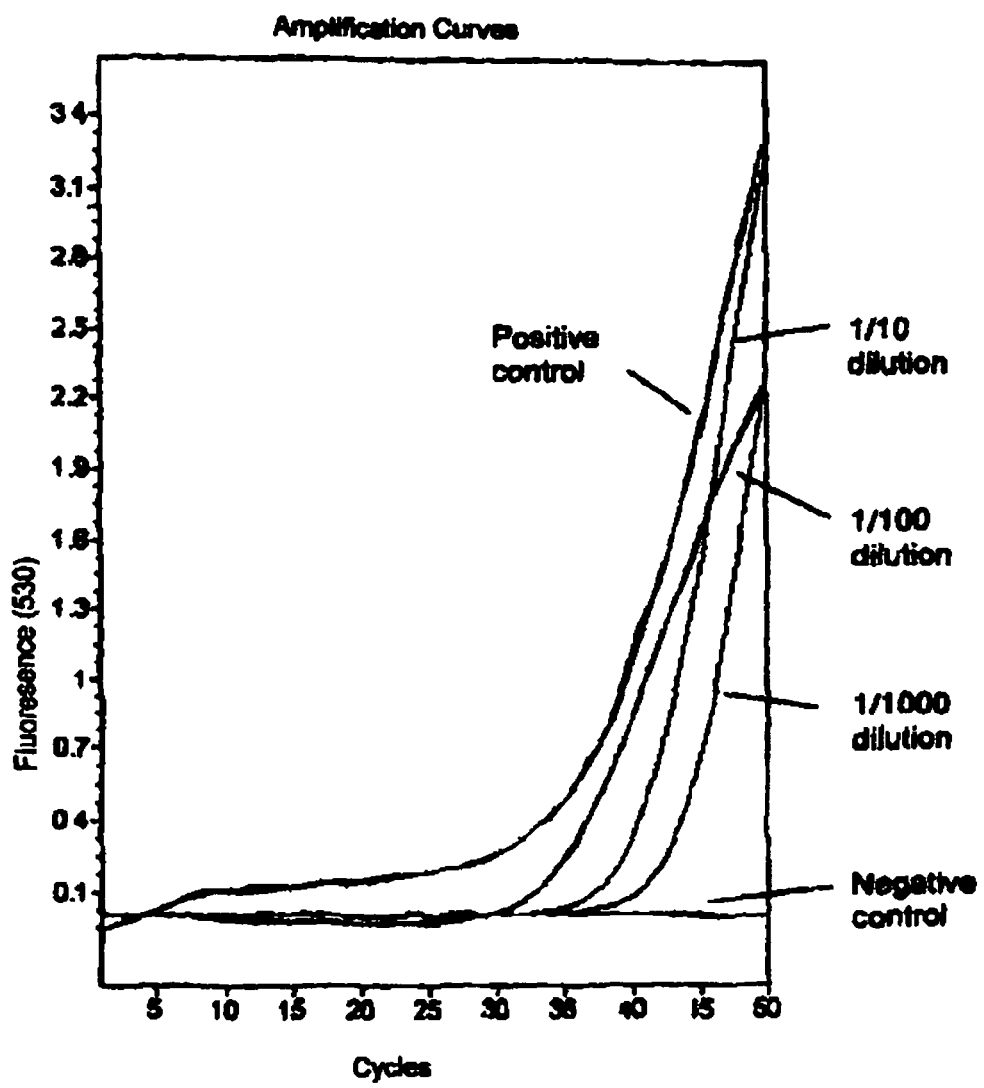
FIG. 5 is a plot of a real-time PCR results for a composition of the invention, comprising an optical reporter linked to a sequenceable DNA molecule.

The results from the RT-PCR experiment are shown in FIG. 5. The results in FIG. 5 show that the 1/100 dilution sample had a Ct of 30, while the 1/10 and 1/1000 dilution had a Ct of 33 and Ct of 36, respectively. At the 1/10 dilution the concentration of the UCP particles is high enough to quench the PCR signal, thus delaying the cycle in which amplification of the target DNA is present.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A sports garment authentication method comprising:
providing the sports garment or a piece of the sports garment, wherein the sports garment or the piece of the sports garment comprises a nucleic acid material having an artificial sequence obtained by digestion and ligation of extracted DNA and having a particular sequence of nucleic acid bases associated with said sports garment, the nucleic acid material being linked by a linking group comprising an alkylene moiety, to an upconverting phosphor particle;
obtaining a sample of said particular nucleic acid material;
detecting the particular sequence of nucleic acid bases of the nucleic acid material by performing a polymerase chain reaction (PCR) on the nucleic acid material; and
verifying said sports garment or piece of said sports garment is genuine by detecting said particular sequence of nucleic acid bases of the nucleic acid material obtained from said sports garment or said piece of sports garment.

2. The method of claim 1 wherein the nucleic acid material is applied to the surface of the piece of the sports garment.

3. The method of claim 1 wherein the nucleic acid material is applied to a specific area on the surface of the piece of the sports garment.

4. The method of claim 3 wherein said marking comprises an indicia or a logo.

5. The method of claim 1 wherein the piece of the sports garment is selected from the group consisting of a sport bib, a racing bib, and a removable sports identification patch.

6. The method of claim 1 wherein the nucleic acid material is deoxyribonucleic acid (DNA).

7. The method of claim 1 wherein the nucleic acid material is ribonucleic acid (RNA).

8. A method for authenticating sports garment comprising the steps of:
providing a sports garment having an associated optical reporter marker, the optical reporter marker having at least one light emitting upconverting phosphor particle linked by a linking group comprising an alkylene moiety, to at least one nucleic acid material having an artificial sequence obtained by digestion and ligation of extracted DNA, the nucleic acid material having an identifiable portion,
detecting the optical reporter marker associated with the garment with a light source,
obtaining a sample of the optical reporter marker from the garment of interest for analysis; and
analyzing the collected sample to detect the presence of the identifiable portion of the nucleic acid material linked to the upconverting phosphor particle.

9. The method of claim 8, wherein the optical reporter marker has the composition of the formula I:

$$(cOpR)\text{-}[L\text{-}(NA)]_m \qquad \qquad I$$

wherein:
m is an integer greater than 1;
(cOpR) is a coated optical reporter particle;
(NA) is a nucleic acid oligomer of the nucleic acid material of detectable sequence; and
L is the linking group covalently bound to the coated optical reporter particle and to the nucleic acid material.

10. The method of claim 9, wherein (NA) is a single stranded DNA molecule having a length of from about 40 bases to about 1000 bases, or a double stranded DNA molecule having a length of from about 40 base pairs to about 1000 base pairs.

11. The method of claim 9, wherein L comprises a $C_{2-8}$ alkylene moiety having a first end covalently bound to the coated optical reporter particle and a second end covalently bound to the nucleic acid oligomer.

12. The method of claim 9, wherein the (UCP) upconverting phosphor particle is of the formula:

$Y_xYb_yEr_zO_2S$; or $Na(Y_xYb_yEr_z)F_4$;

wherein:
x is from about 0.6 to about 0.95;
y is from about 0.05 to about 0.35; and
z is from about 0.1 to about 0.001.

13. The method of claim 9, wherein L is of the formula:

-A-R$^1$—B— wherein:
R$^1$ is C$_{2-8}$alkylene;
-A- is a group covalently bonded to the surface of the coated optical reporter; and
—B— is a group covalently bonded to the 3' or 5' end of the nucleic acid oligomer.

14. A method for authenticating a sports garment comprising the steps of:
providing a sports garment having an associated optical reporter marker, the optical reporter marker having at least one light emitting upconverting phosphor particle linked by a linking group comprising an alkylene moiety, to a nucleic acid taggant, the nucleic acid taggant having a plurality of artificial polymorphic double stranded (ds) DNA fragments each having an artificial sequence obtained by restriction digestion and ligation of extracted DNA, said artificial polymorphic dsDNA fragments having an identifiable portion,
detecting the optical reporter marker associated with the sports garment with a light source,
obtaining a sample of the optical reporter marker from the sports garment for analysis,
analyzing the sample to detect the presence of the identifiable portion of the artificial polymorphic (ds)DNA fragments linked to the upconverting phosphor particle by performing a polymerase chain reaction (PCR) on the collected sample comprising said artificial polymorphic (ds)DNA fragments using specific primers, thereby producing specific length amplicons; and
verifying that the sports garment is genuine by detecting the specific lengths of said specific length amplicons amplified from said artificial polymorphic dsDNA fragments in said sports garment.

15. The method of claim 14, wherein the optical reporter marker linked to the plurality of artificial polymorphic double stranded (ds)DNA fragments has the composition of the formula I:

(cOpR)-[L-(NA)]$_m$         I wherein:
m is an integer greater than 1;
(cOpR) is a coated optical reporter particle, said COpR having an upconverting phosphor (UCP) material;
(NA) is a nucleic acid oligomer of detectable sequence, wherein (NA) is a single stranded DNA molecule having a length of between about 40 bases and about 1000 bases, or a double stranded DNA molecule having a length of between about 40 base pairs and about 1000 base pairs; and
L is a linking group covalently bound to the coated optical reporter particle and to the nucleic acid oligomer, wherein L has an alkylene moiety.

16. The method of claim 15, wherein (NA) is a single stranded DNA molecule having a length of between about 100 bases and about 800 bases, or a double stranded DNA molecule having a length of between about 150 base pairs and about 500 base pairs.

17. The method of claim 15, wherein the (UCP) upconverting phosphor particle is of the formula:

$Y_xYb_yEr_zO_2S$; or $Na(Y_xYb_yEr_z)F_4$;

wherein:
x is from about 0.6 to about 0.95;
y is from about 0.05 to about 0.35; and
z is from about 0.1 to about 0.001.

18. The method of claim 15, wherein L is of the formula:

-A-R$^1$—B— wherein:
R$^1$ is C$_{2-8}$alkylene;
-A- is a group covalently bonded to the surface of the coated optical reporter; and
—B— is a group covalently bonded to the 3' or 5' end of the nucleic acid oligomer.

19. The method of claim 18, wherein -A- is —O—.

20. The method of claim 18, wherein —R$^1$— is —(CH$_2$)$_n$— and wherein n is from 2 to 8.

21. The method of claim 18, wherein —B— is:
—S—;
—O—;
—NR$^a$—;
—S—(CH$_2$)$_p$—;
—O—(CH$_2$)$_p$—;
—NR$^a$—(CH$_2$)$_p$—;
—S—(CH$_2$)$_q$—C(O)—NR$^a$—(CH$_2$)$_p$—;
—O—(CH$_2$)$_q$—C(O)—NR$^a$—(CH$_2$)$_p$—;
—NR$^a$—(CH$_2$)$_q$—C(O)—NR$^a$—(CH$_2$)$_p$—;
—S—C(O)—(CH$_2$)$_r$—C(O)—NR$^a$—(CH$_2$)$_p$—;
—O—C(O)—(CH$_2$)$_r$—C(O)—NR$^a$—(CH$_2$)$_p$—; or
—NR$^a$—C(O)—(CH$_2$)$_r$—C(O)—NR$^a$—(CH$_2$)$_p$—;

wherein:
p is from 2 to 8;
q is from 1 to 8;
r is from 2 to 8; and
each R$^a$ is independently hydrogen or C$_{1-6}$alkyl.

22. The method of claim 18, wherein —B— is:
—S—(CH$_2$)$_q$—C(O)—NR$^a$—(CH$_2$)$_p$ or
—NR$^a$—C(O)—(CH$_2$)$_r$—C(O)—NR$^a$—(CH$_2$)$_p$—.

23. The method of claim 22, wherein:
p is from 2 to 6;
q is from 1 to 3; and
r is 2 or 3.

24. The method of claim 18, wherein —B— is:
—S—CH$_2$—C(O)—NH—(CH$_2$)$_6$—; or
—NH—C(O)—(CH$_2$)$_3$—C(O)—NH—(CH$_2$)$_6$—.

25. The method of claim 18, wherein the cOpR is coated with silica.

26. The method of claim 25, wherein cOpR is a coated optical reporter particle having an upconverting phosphor (UCP) material comprising Yttrium oxysulfide.

27. The method of claim 14, wherein the optical reporter marker has the composition of the formula II:

(UCP)-[A-R$^1$—X—R$^2$—C(O)—NR$^a$—R$^3$-(DNA)]$_m$     II wherein:
m is an integer greater than 1;
UCP is an upconverting phosphor particle;
DNA is a double stranded deoxyribonucleic acid fragment;

-A- is a group capable of covalently bonding to the surface of the Upconverting phosphor particle;
$R^1$ is $C_{2-8}$alkylene,
$R^2$ is $C_{1-8}$alkylene or —C(O)—$C_{1-8}$alkylene-;
—X— is —O—, —S— or —$NR^a$—;
$R^3$ is $C_{2-8}$alkylene; and
$R^a$ is hydrogen or $C_{1-6}$alkyl.

28. The method of claim 27, wherein the optical reporter marker has the composition of the formula IV:

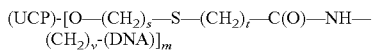

(UCP)-[O—(CH$_2$)$_s$—S—(CH$_2$)$_t$—C(O)—NH—(CH$_2$)$_v$-(DNA)]$_m$        IV wherein:
s is from 2 to 6;
v is from 2 to 6;
t is from 1 to 3.

29. The method of claim 27, wherein the optical reporter marker has the composition of the formula V:

(UCP)-[O—(CH$_2$)$_s$—NH—C(O)—(CH$_2$)$_u$—C(O)—NH—(CH$_2$)$_v$-(DNA)]$_m$        V wherein:
s is from 2 to 6;
v is from 2 to 6;
u is 2 or 3.

30. The method of claim 27, wherein the optical reporter marker has the composition of the formula VI:

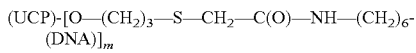

(UCP)-[O—(CH$_2$)$_3$—S—CH$_2$—C(O)—NH—(CH$_2$)$_6$-(DNA)]$_m$        VI.

31. The method of claim 27, wherein the optical reporter marker has the composition of the formula VII:

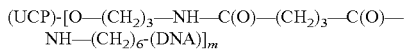

(UCP)-[O—(CH$_2$)$_3$—NH—C(O)—(CH$_2$)$_3$—C(O)—NH—(CH$_2$)$_6$-(DNA)]$_m$        VII.

32. The method of claim 15, wherein the cOpR comprises a visually detectable light emitting material selected from the group consisting of a fluorescent dye, a upconverting phosphor, a rare earth doped-ceramic powder, and a quantum dot.

33. The method of claim 32, wherein said light emitting material is excitable by UV or infrared light.

34. The method of claim 15, wherein the cOpR comprises at least one electromagnetic radiation-emitting material.

35. The composition of claim 34, where the electromagnetic radiation-emitting material is detectable using a device which selected from the group consisting of an infrared radiation source, a magnetic field source, a quantum dot and an electromagnetic pulse source.

36. The method of claim 14, wherein the nucleic acid taggant is ds DNA.

37. The method of claim 14, wherein the sports garment is selected from the group of a manufactured sporting good, a sport bib, a hat, sport logo on fabric, sport shorts, and a wash tag on a sporting good.

38. The method of claim 14, wherein said authenticating further comprises associating the optical reporter marker with the sports garment in a database management system.

39. A method for authenticating a sports garment, comprising:
providing a optical reporter marker linked by a linking group comprising an alkylene moiety, to at least one nucleic acid taggant;
applying the marker compound to at least one sports garment, which sports garment enters at least one supply chain;
locating and collecting a sample of the optical reporter marker from said sports garment after said sports garment has entered said supply chain; and
identifying said nucleic acid taggant from said sports garment.

40. A kit for authenticating sports garment comprising:
a container comprising an optical reporter marker linked by a linking group comprising an alkylene moiety, to at least one nucleic acid taggant; and
an applicator for applying a sample of the optical reporter to the sports garment.

41. A method for authenticating a sports garment comprising the steps of;
providing a sports garment having an associated optical reporter marker, the optical reporter marker having at least one light emitting upconverting phosphor particle covalently linked by a linking group comprising an alkylene moiety, to a nucleic acid taggant, the nucleic acid taggant having a plurality of polymorphic DNA fragments each having an artificial sequence obtained by restriction digestion and ligation of extracted DNA, at least one of said polymorphic DNA fragments having an identifiable portion,
detecting the optical reporter marker associated with the sports garment with a light source,
obtaining a sample of the optical reporter marker from the sports garment for analysis,
analyzing the collected sample to detect the presence of the identifiable portion of the at least one polymorphic DNA fragment having an identifiable portion and covalently linked to the upconverting phosphor particle by performing a polymerase chain reaction (PCR) with specific primers to produce specific amplicons and hybridizing the specific amplicons with a probe specific to the identifiable portion; and
thereby verifying that the sports garment is genuine by detecting said identifiable portion in the specific amplicons.

42. The method of claim 14, wherein said artificial polymorphic dsDNA fragments having an identifiable portion are non-heritable DNA fragments.

43. The method of claim 14, wherein the detecting the specific lengths of said specific length amplicons amplified from said artificial polymorphic dsDNA fragments in said sports garment comprises a capillary electrophoresis step.

44. The method of claim 41, wherein said at least one polymorphic DNA fragment having an identifiable portion is a non-heritable DNA fragment.

45. The method of claim 41, wherein the probe specific to the identifiable portion of the polymorphic DNA fragment is a fluorescent probe.

* * * * *